US010468121B2

(12) United States Patent
Kermani et al.

(10) Patent No.: US 10,468,121 B2
(45) Date of Patent: Nov. 5, 2019

(54) PHASING AND LINKING PROCESSES TO IDENTIFY VARIATIONS IN A GENOME

(71) Applicant: Complete Genomics, Inc., Mountain View, CA (US)

(72) Inventors: Bahram Ghaffarzadeh Kermani, Los Altos, CA (US); Radoje Drmanac, Los Altos Hills, CA (US); Brock A. Peters, San Francisco, CA (US)

(73) Assignee: Complete Genomics, Inc., San Jose, CA (US)

( * ) Notice: Subject to any disclaimer, the term of this patent is extended or adjusted under 35 U.S.C. 154(b) by 1279 days.

(21) Appl. No.: 14/503,872

(22) Filed: Oct. 1, 2014

(65) Prior Publication Data

US 2015/0094961 A1 Apr. 2, 2015

Related U.S. Application Data

(60) Provisional application No. 61/885,470, filed on Oct. 1, 2013.

(51) Int. Cl.
*G16B 30/00* (2019.01)
*G16B 20/00* (2019.01)
*G06F 19/10* (2011.01)

(52) U.S. Cl.
CPC .................................. *G16B 30/00* (2019.02)

(58) Field of Classification Search
None
See application file for complete search history.

(56) References Cited

U.S. PATENT DOCUMENTS

| 8,592,150 B2 | 11/2013 | Drmanac |
| 2013/0054151 A1 | 2/2013 | Kermani et al. |
| 2013/0054508 A1 | 2/2013 | Kermani et al. |
| 2013/0059740 A1 | 3/2013 | Drmanac |
| 2013/0096841 A1 | 4/2013 | Kermani et al. |
| 2013/0124100 A1 | 5/2013 | Drmanac |

FOREIGN PATENT DOCUMENTS

WO 2015/010051 A1 1/2015

OTHER PUBLICATIONS

PCT/US2014/058648 , "International Preliminary Report on Patentability", dated Apr. 14, 2016, 11 pages.
PCT/US2014/058648 , "Invitation to Pay Additional Fees and Partial Search Report", dated Jan. 22, 2015, 3 pages.
International Search Report and Written Opinion dated Mar. 26, 2015 in PCT/US2014/058648, 15 pages.

*Primary Examiner* — Lori A. Clow
(74) *Attorney, Agent, or Firm* — Kilpatrick Townsend & Stockton LLP

(57) ABSTRACT

Long fragment read techniques can be used to identify deletions and resolve base calls by utilizing shared labels (e.g., shared aliquots) of a read with any reads corresponding to heterozygous loci (hets) of a haplotype. For example, the linking of a locus to a haplotype of multiple hets can increase the reads available at the locus for determining a base call for a particular haplotype. For a hemizygous deletion, a region can be linked to one or more hets, and the labels for a particular haplotype can be used to identify which reads in the region correspond to which haplotype. In this manner, since the reads for a particular haplotype can be identified, a hemizygous deletion can be determined. Further, a phasing rate of pulses can be used to identify large deletions. A deletion can be identified with the phasing rate is sufficiently low, and other criteria can be used.

23 Claims, 21 Drawing Sheets

Comparison of sequencing performance between different genome assemblies

| Sample | Library type | % genome fully called | # of high quality SNPs called | # of high quality indels called | # of high quality heterozygous SNPs called | # of heterozygous phased SNPs | # cells as determined by fragment coverage |
|---|---|---|---|---|---|---|---|
| Embryo #2 | Standard | 87% | 2,852,126 | 315,028 | 1,324,910 | N/A | N/A |
| Embryo #5 Replicate 1 | Standard | 95% | 3,251,203 | 429,952 | 1,810,413 | N/A | N/A |
| Embryo #5 Replicate 2 | Standard | 92% | 3,050,097 | 323,579 | 1,574,621 | N/A | N/A |
| Embryo #7 | Standard | 95% | 3,247,236 | 378,154 | 1,830,604 | N/A | N/A |
| Embryo #9 | Standard | 88% | 2,280,061 | 280,658 | 48,204 | N/A | N/A |
| Embryo #10 Regular Coverage | Standard | 91% | 2,922,885 | 293,650 | 1,410,649 | N/A | N/A |
| Embryo #10 High Coverage | Standard | 95% | 3,216,337 | 375,496 | 1,768,650 | N/A | N/A |
| Embryo #10 Very High Coverage | Standard | 97% | 3,307,510 | 425,334 | 1,909,534 | N/A | N/A |
| Unamplified control genome of European decent[T] | Standard | 96% | 3,383,960 | 455,833 | 2,007,998 | N/A | N/A |
| Embryo #8 Replicate 1 | LFR | 96% | 3,426,247 | 407,979 | 2,073,432 | 2,159,514 | 10 |
| Embryo #8 Replicate 2 | LFR | 95% | 3,351,395 | 408,837 | 1,939,778 | 2,102,173 | 4 |
| Embryo #13 | LFR | 95% | 3,343,716 | 432,422 | 1,927,103 | 1,959,122 | 4 |
| Leukocyte library | LFR | 88% | 3,057,647 | 284,553 | 1,611,031 | 1,652,138 | 5 |
| NA19240* | LFR | 94% | 3,751,078 | 419,754 | 2,410,575 | 2,578,903 | 12 |
| NA12892* | LFR | 92% | 3,130,825 | 331,376 | 1,900,711 | 1,917,442 | 23 |

Table 300 (cont'd)

| Sample | Mitochondrial genome read coverage (X) | DNA bases sequenced (Gb) | N50 contig length (kb) | % Genome covered by contigs | Original Myotonic dystrophy diagnosis | LFR Myotonic dystrophy diagnosis | Sex |
|---|---|---|---|---|---|---|---|
| Embryo #2 | 2,928 | 213 | N/A | N/A | Unaffected | No diagnosis | Female |
| Embryo #5 Replicate 1 | 6,446 | 391 | N/A | N/A | Affected | No diagnosis | Male |
| Embryo #5 Replicate 2 | 4,708 | 213 | N/A | N/A | Affected | No diagnosis | Male |
| Embryo #7 | 3,923 | 224 | N/A | N/A | No diagnosis | No diagnosis | Male |
| Embryo #9 | 6,144 | 158 | N/A | N/A | No diagnosis | No diagnosis | Female |
| Embryo #10 Regular Coverage | 17,011 | 143 | N/A | N/A | No diagnosis | No diagnosis | Male |
| Embryo #10 High Coverage | 30,376 | 260 | N/A | N/A | No diagnosis | No diagnosis | Male |
| Embryo #10 Very High Coverage | 50,519 | 429 | N/A | N/A | No diagnosis | No diagnosis | Male |
| Unamplified control genome of European decent[1] | 1,806 | 189 | N/A | N/A | N/A | N/A | Female |
| Embryo #8 Replicate 1 | 105,607 | 379 | 586 | 79% | No diagnosis | Unaffected | Female |
| Embryo #8 Replicate 2 | 89,378 | 391 | 519 | 76% | No diagnosis | Unaffected | Female |
| Embryo #13 | 46,721 | 390 | 459 | 75% | Affected | Affected | Female |
| Leukocyte library | 637 | 272 | 359 | 63% | N/A | N/A | Female |
| NA19240* | 4,839 | 509 (LFR) +176 (STD) | 1,282 | 88% | N/A | N/A | Female |
| NA12892* | 2,888 | 284 (LFR) +213 (STD) | 553 | 74% | N/A | N/A | Female |

FIG. 3 (cont'd)

Position #2

|   | A | C | G | T |
|---|---|---|---|---|
| A |   |   |   |   |
| C | 4 | 4 |   |   |
| G |   | 6 |   |   |
| T |   |   |   |   |

Position #1

FIG. 7A    700

Position #2

|   | A | C | G | T |
|---|---|---|---|---|
| A |   |   |   |   |
| C | 2 |   |   |   |
| G |   | 1 |   |   |
| T |   |   |   |   |

Position #1

FIG. 7B    750

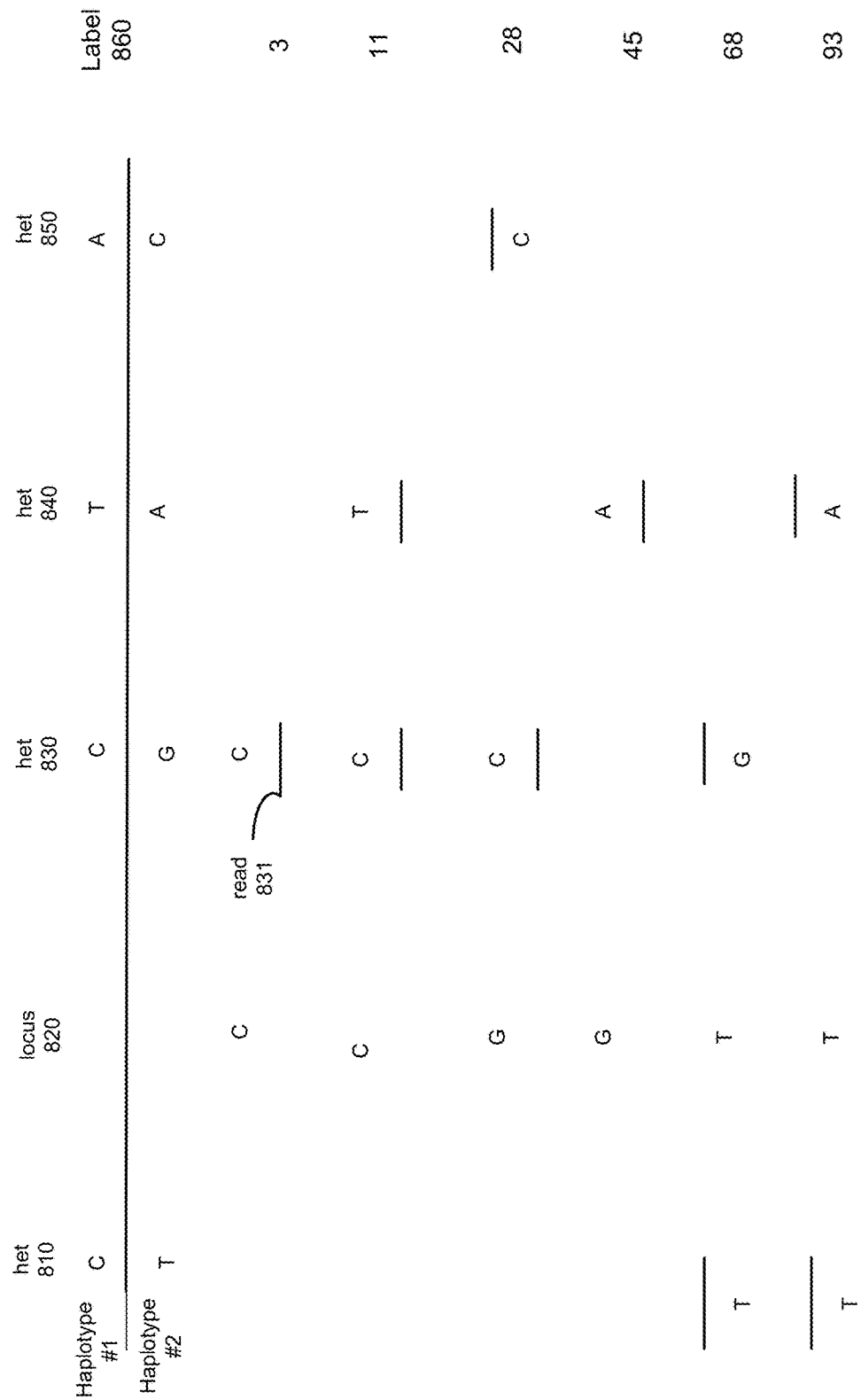

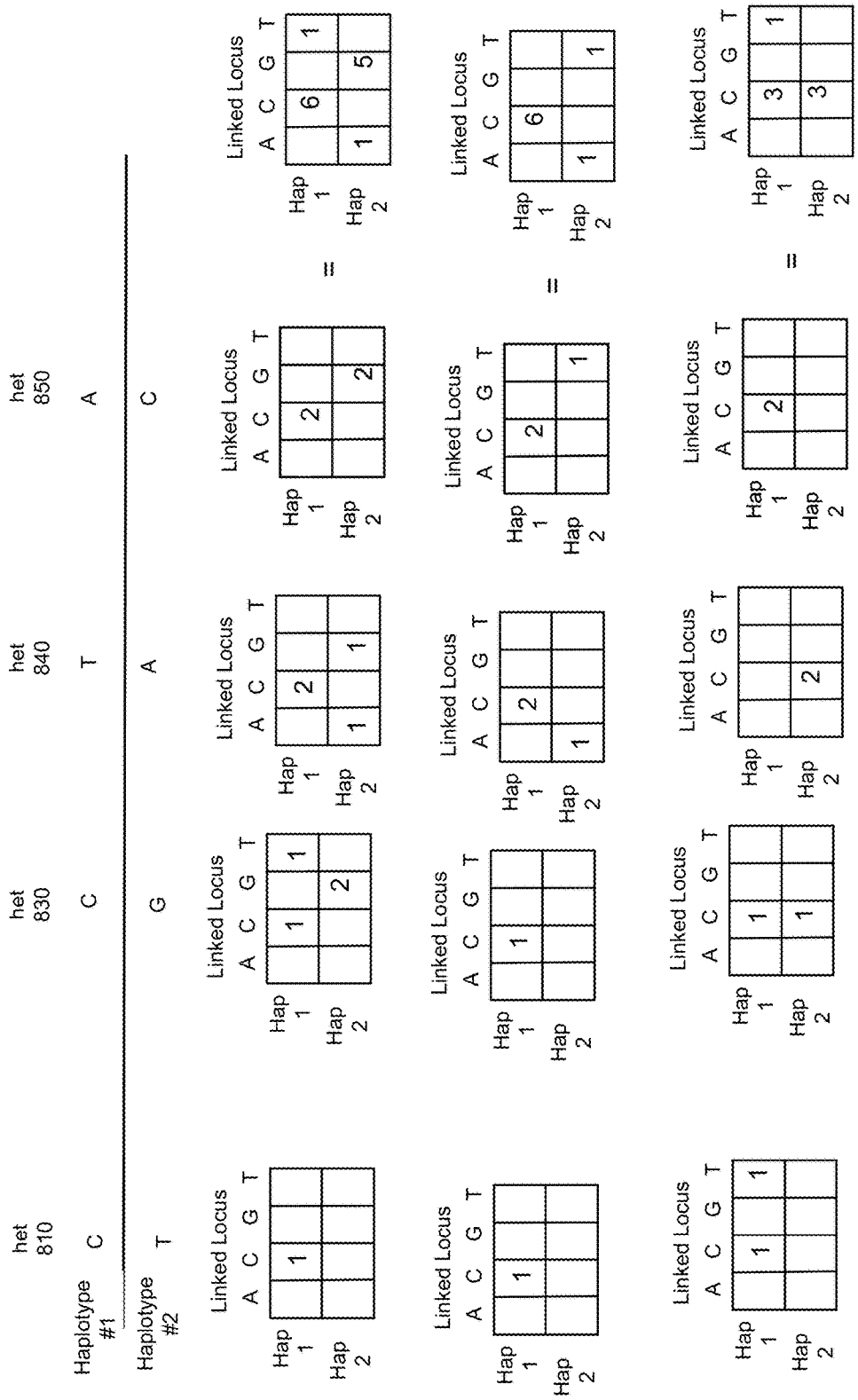

Linked Locus

|  | A | C | G | T |
|---|---|---|---|---|
| Haplotype 1 | 18 | 4 |  |  |
| Haplotype 2 |  | 22 |  |  |

Linked Locus

|  | A | C | G | T |
|---|---|---|---|---|
| Haplotype 1 | 4 | 18 |  |  |
| Haplotype 2 |  | 22 |  |  |

PHASING AND LINKING PROCESSES TO IDENTIFY VARIATIONS IN A GENOME

CROSS-REFERENCES TO RELATED APPLICATIONS

The present application claims priority from and is a nonprovisional application of U.S. Provisional Application No. 61/885,470, entitled "PHASING AND LINKING PROCESSES TO IDENTIFY VARIATIONS IN A GENOME" filed Oct. 1, 2013, the entire contents of which are herein incorporated by reference for all purposes.

This application is related to commonly owned U.S. patent application Ser. No. 13/448,279, entitled "Sequencing Small Amounts Of Complex Nucleic Acids", filed Apr. 16, 2012; U.S. patent application Ser. No. 13/447,087, entitled "Processing And Analysis Of Complex Nucleic Acid Sequence Data", filed Apr. 13, 2012; U.S. patent application Ser. No. 13/649,966, entitled "Identification Of DNA Fragments And Structural Variations", filed Oct. 11, 2012; U.S. patent application Ser. No. 13/591,723, entitled "Phasing Of Heterozygous Loci To Determine Genomic Haplotypes", filed Aug. 22, 2012; and U.S. patent application Ser. No. 13/591,741, entitled ""Analyzing Genome Sequencing Information To Determine Likelihood Of Co-Segregating Alleles On Haplotypes", filed Aug. 22, 2012, the disclosures of which are incorporated by reference in their entirety

BACKGROUND

Worldwide, over 5 million babies have been born through in vitro fertilization (IVF) since the birth of the first in 1978. Exact numbers are difficult to determine, but it has been estimated that currently 350,000 babies are born yearly through IVF. That number is expected to rise as older maternal age is associated with decreased fertility rates and women in developed countries continue to delay childbirth to later ages. In 95% of IVF procedures, no diagnostic testing of the embryos is performed (wide web at sart.org/find_frm.html). Couples with prior difficulties conceiving or those wishing to avoid the transmission of highly penetrant heritable diseases often choose to perform pre-implantation genetic diagnosis (PGD). PGD involves the biopsy of 1 cell from a 3 day embryo or up to 10 cells at the 5-6 day blastocyst stage followed by genetic analysis. Currently this is either an assay for translocations and the correct chromosome copy number, a unique test designed and validated for each specific heritable disease, or a combination of both. Importantly, none of these approaches can detect de novo mutations or variations that have yet to be associated with a particular disease.

Currently, the only methods available for pre-implantation genetic diagnosis (PGD) of in vitro fertilized embryos are those detecting large genomic alterations or single-gene disorders. These methods can be blind to a large number of potential genomic defects.

While there has been some dispute in the literature regarding the role of IVF in birth defects, two recent studies claim to see an increased incidence in children born through IVF, which could be caused by an excess of genetic defects in these infertile patients. In addition, advanced maternal age has been linked to an increase in aneuploid embryos and advanced paternal age to embryonic de novo mutations. Many recent large scale sequencing studies have found that de novo variations spread across many different genes are likely to be the cause of a large fraction of Autism cases, as well as many other rare congenital disorders. These studies suggest we could be doing more to try to improve the health of IVF newborns.

Current targeted approaches to PGD would miss many important functional changes within the embryonic DNA sequence. Importantly, even a comprehensive WGS-based carrier screen of both parents would not enable targeted pre-implantation or prenatal diagnoses due to de novo mutations. A recent report found that de novo mutations affect functional regions of the genome more often than regions not known to have a function, further underlining the importance of being able to identify this class of genomic variations in PGD. Further, the identification of mutations can useful for a variety of purposes besides for IVF.

Therefore, it is desirable to provide improved techniques for determining mutations in a genome.

BRIEF SUMMARY

Embodiments provide systems, methods, and apparatuses to perform phasing and linking processes for identifying a haplotype of a genome of an organism, which may involve identifying variations in the genome. Such variations can include a hemizygous deletion (i.e., a deletion in one haplotype at a given location/region), a deletion in both haplotypes in a region, or an insertion. Embodiments can use long fragment reads (LFR) to determine that two reads are likely from a same long fragment when they have a same label (e.g., from a same aliquots) and are within a certain distance of each other (e.g. 50 Kb).

In one example, embodiments are directed to resolving base calls (e.g., from a no-call to a base call or to correct base calls). Embodiments can provide greater accuracy by performing phasing to determine haplotypes. Then, long fragment reads (LFR) techniques can be used to resolve base calls by utilizing shared labels (e.g., shared aliquots) of a read with any reads corresponding to a haplotype. The linking of a locus to a haplotype of multiple heterozygous loci (hets) can help to utilize many of the reads available at the locus.

In another example, long fragment reads (LFR) techniques can be used to identify deletions. For a hemizygous deletion, a region can be linked to one or more hets, and the labels for a particular haplotype can be used to identify which reads in the region correspond to which haplotype. In this manner, since the reads for a particular haplotype can be identified, a hemizygous deletion can be determined with greater accuracy when the amount of reads for the particular haplotype is low. Such a determination can give greater accuracy than using an amount of all reads in the region.

In another example, a phasing rate of pulses (a contiguous section of the reference genome covered by sequence reads having a same label) can be used to identify large deletions. A phasing rate of a region can be determined from a total number of pulses for a region and a number of pulses that cover a phased het. A deletion can be identified with the phasing rate is sufficiently low.

Other embodiments are directed to systems, portable consumer devices, and computer readable media associated with methods described herein.

A better understanding of the nature and advantages of embodiments of the present invention may be gained with reference to the following detailed description and the accompanying drawings.

BRIEF DESCRIPTION OF THE DRAWINGS

FIG. 3 shows a table 300 of comparison of sequencing performance according to embodiments of the present invention.

FIG. 7A shows a connectivity matrix 700 having inconsistent data. FIG. 7B shows a connectivity matrix 750 having a low number of reads.

FIG. 8A shows a diagram 800 of a process of linking a locus 820 to multiple hets. FIG. 8B illustrates a process of using linking a locus to multiple hets to change no calls (N) to base calls according to embodiments of the present invention.

FIG. 9A is a matrix 900 illustrating the linking of the locus to the two haplotypes. FIG. 9B is a matrix 950 illustrating the linking of the locus to the two haplotypes

DEFINITIONS

Figure 1:
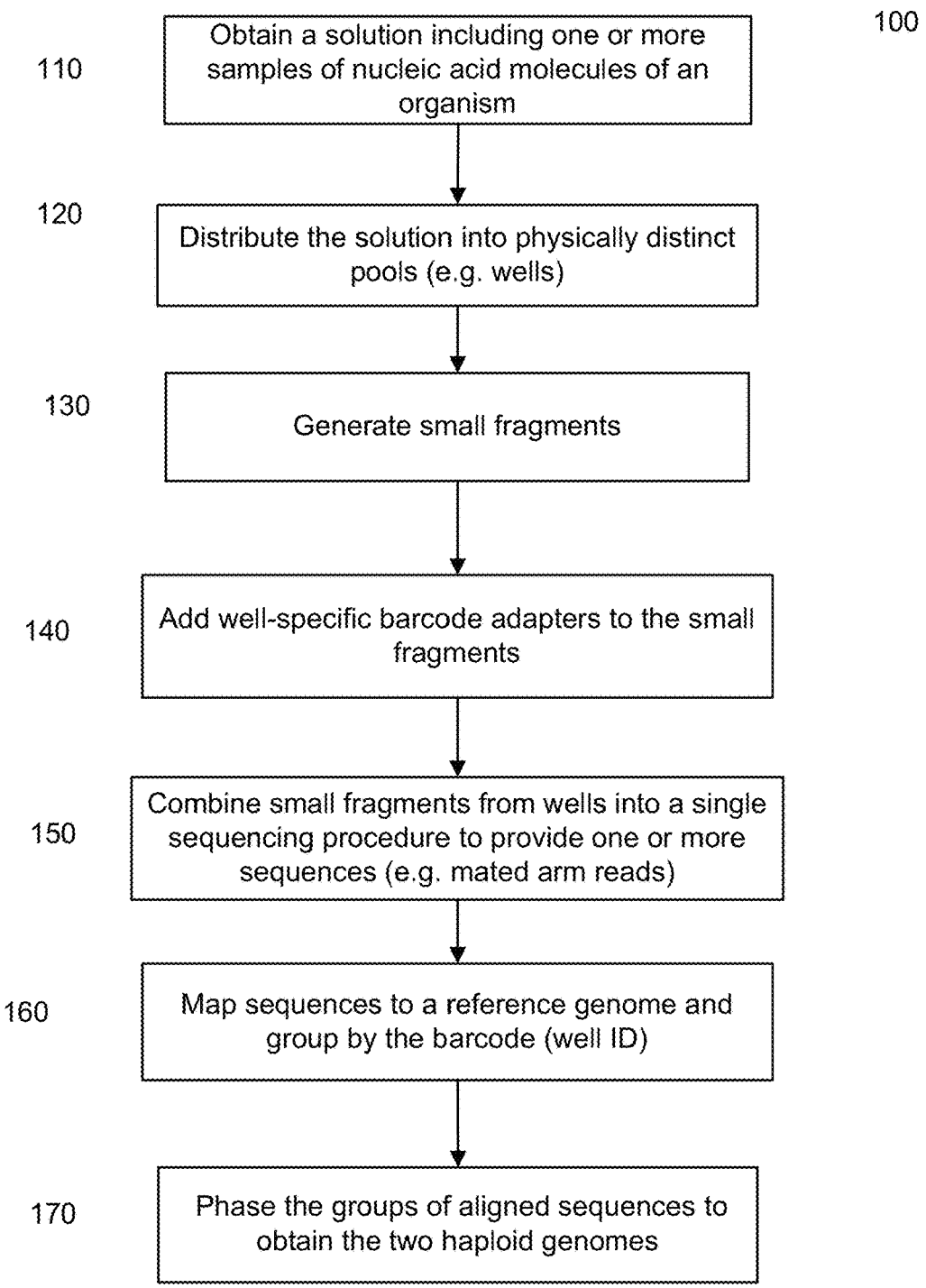
FIG. 1 is a flowchart illustrating a method 100 for obtaining short sequence reads for assembling into long fragments according to embodiments of the present invention.

The following definitions may be helpful in providing background for an understanding of embodiments of the invention.

A "sequence read" or "read" refers to data representing a sequence of monomer units (e.g., bases) that comprise a nucleic acid molecule (e.g., DNA, cDNA, RNAs including mRNAs, rRNAs, siRNAs, miRNAs and the like). The sequence read can be measured from a given molecule via a variety of techniques.

As used herein, a "fragment" refers to a nucleic acid molecule that is in a biological sample. Fragments can be referred to as long or short, e.g., fragments longer than 10 Kb (e.g. between 50 Kb and 100 Kb) can be referred to as long, and fragments shorter than 1,000 bases can be referred to as short. A long fragment can be broken up into short fragments, upon which sequencing is performed.

A "mate pair" or "mated reads" or "paired-end" can refer to any two reads from a same molecule that are not fully overlapped (i.e., cover different parts of the molecule). Each of the two reads would be from different parts of the same molecule, e.g., from the two ends of the molecule. As another example, one read could be for one end of the molecule in the other read for a middle part of the molecule. As a genetic sequence can be ordered from beginning to end, a first read of a molecule can be identified as existing earlier in a genome than the second read of the molecule when the first read starts and/or ends before the start and/or end of the second read. Two reads can be referred to as being different arm reads when the two reads are from different parts of the same molecule. More than two reads can be obtained for each molecule, where each read would be for different part of the molecule. Usually there is a gap (mate gap) from about 100-10,000 bases of unread sequence between two reads. Examples of mate gaps include 500+/−200 bases and 1000+/−300 bases.

The small fragments that originate from a same long fragment can have a same "label" that identifies an origin for small fragment. An example of a label is "Well ID," which refers to a bar code or tag that is added to a small fragment to determine which well the read comes from. Such an example is applicable when long fragments are distributed into multiple wells, or other types of aliquots, and then fragmented into smaller fragments. A tag for each read is decoded (corrected) and projected into a unique tag. Another example of a label can be found in U.S. Provisional Application No. 61/801,052, where a same label can be affixed to different segments of a same long fragment.

"Mapping" or "aligning" refers to a process which relates a read (or a pair of reads) to zero, one, or more locations in the reference to which the arm read is similar, e.g., by matching the instantiated arm read to one or more keys within an index corresponding to a location within a reference As used herein, an "allele" corresponds to one or more nucleotides (which may occur as a substitution or an insertion) or a deletion of one or more nucleotides. A "locus" corresponds to a location in a genome. For example, a locus can be a single base or a sequential series of bases. The term "genomic position" can refer to a particular nucleotide position in a genome or a contiguous block of nucleotide positions. A "heterozygous locus" (also called a "het") is a location in a reference genome or a specific genome of the organism being mapped, where the copies of a chromosome do not have a same allele (e.g. a single nucleotide or a collection of nucleotides). A "het" can be a single-nucleotide polymorphism (SNP) when the locus is one nucleotide that has different alleles. A "het" can also be a location where there is an insertion or a deletion (collectively referred to as an "indel") of one or more nucleotides or one or more tandem repeats. A single nucleotide variation (SNV) corresponds to a genomic position having a nucleotide that differs from a reference genome for a particular person. An SNV can be homozygous for a person if there is only one nucleotide at the position, and heterozygous if there are two alleles at the position. A heterozygous SNV is a het. SNP and SNV are used interchangeably herein.

"Phasing" refers to identifying alleles of different hets as being on a same haplotype. Phasing can include determining which chromosome alleles of different hets are on. A "contig" refers to a contiguous section of a chromosome defined by a plurality of connected hets, where a contig would have two haplotypes for a diploid organism. Contigs can be phased to determine a copy of a chromosome. A "pulse" corresponds to a reconstruction of a long fragment, e.g., as can be determined by analyzing a coverage histogram of reads of a same aliquot aligned to a same region of a reference.

"Linking" refers to identifying sequence reads as being on a same haplotype as a specific allele of a het. A read can be identified as being on a same haplotype by being from a same aliquot as the allele of the het. A "Well ID" refers to a bar code or tag that is added to a small fragment to determine which well (aliquot) a sequence read comes from. Small fragments with a same well ID can be used to reassemble a long fragment. A "phase het" is a het that is used in phasing to determine a contig.

An amplification (e.g., a duplication) can be considered an insertion, as the extra copy of the region can be inserted consecutive with the original copy or inserted into another place in the genome. As used herein, the term "chromosome" includes copies of DNA (e.g., as occur in animals) or copies of RNA (e.g., as may occur in viruses). A hemizygous deletion corresponds to part of one chromosome being deleted. A hemizygous amplification corresponds to part of one chromosome being amplified to exist more than once in the genome.

DETAILED DESCRIPTION

The identification of deletions in only one chromosome can be difficult to identify due to natural variation, e.g., variation of 0.5x-4x in total coverage from one part of the genome to another is much to be expected. Thus, it is difficult to determine a hemizygous deletion just by comparing coverage across different regions, particularly for a low number of cells. Additionally, with a relatively small sample, the number of no-calls can be higher than desired. And, incorrect calls can also be higher than desired.

Embodiments can provide greater accuracy by performing phasing to determine haplotypes. Then, long fragment reads (LFR) techniques can be used to identify deletions and resolve base calls by utilizing shared labels (e.g., shared aliquots) of a read with any reads corresponding to a haplotype. The linking of a locus to a haplotype of multiple heterozygous loci (hets) can help to utilize most, if not all, of the reads available at the locus, as opposed to just a connection between two possible hets. Further, a phasing rate of pulses (a contiguous section of the reference genome covered by sequence reads having a same label) can be used to identify large deletions.

In the examples, we demonstrate the use of an advanced whole genome sequencing (WGS) test that provides an accurate and phased genome sequence from ~10 cells as a screening strategy to identify all potential detrimental defects within the embryonic genome. This will allow for the avoidance of those embryos with inherited and/or de novo genetic defects, as small as a single nucleotide, likely to result in the failure of a live birth or a newborn with a severe genetic disease.

I. LABELS AND PHASING

A label can be used to determine an origin of the nucleic acid molecule (e.g., a long fragment) that the sequence read was obtained. The origin can be a particular nucleic acid molecule, the sequence reads from the same nucleic acid molecule have the same label. As another example, the label can correspond to a particular aliquot (e.g., a well), where each aliquot includes a relatively small percentage of the genome. As explained below, having a relatively small percentage of the genome in an aliquot can allow for an assumption that sequence reads that are similar to each other (e.g., that align to each other or are close to each other in a reference genome) are from a same larger fragment.

A. Example of Labels (Aliquots)

The well that a particular arm read of a fragment is obtained can be tracked. This well ID can be determined using a barcode that is attached to a small fragment. Thus, the origin of the small fragments can be tracked. The following describes various implementations that may be used to assemble reads of short fragments into long fragments of a particular haplotype. For example, heterozygous loci (hets) can be determined, and the labels can be used to determine which alleles of different hets are phased (i.e., which alleles of different hets are on the same haplotype).

FIG. 1 is a flowchart illustrating a method 100 for obtaining short sequence reads for assembling into long fragments to obtain two haplotypes according to embodiments of the present invention. Method 100 will be described in conjunction with FIG. 2, which shows a diagram illustrating steps of method 100. A computer system can perform parts of method 100. Method 100 is illustrative and embodiments can use variations of method 100.

Figure 2:
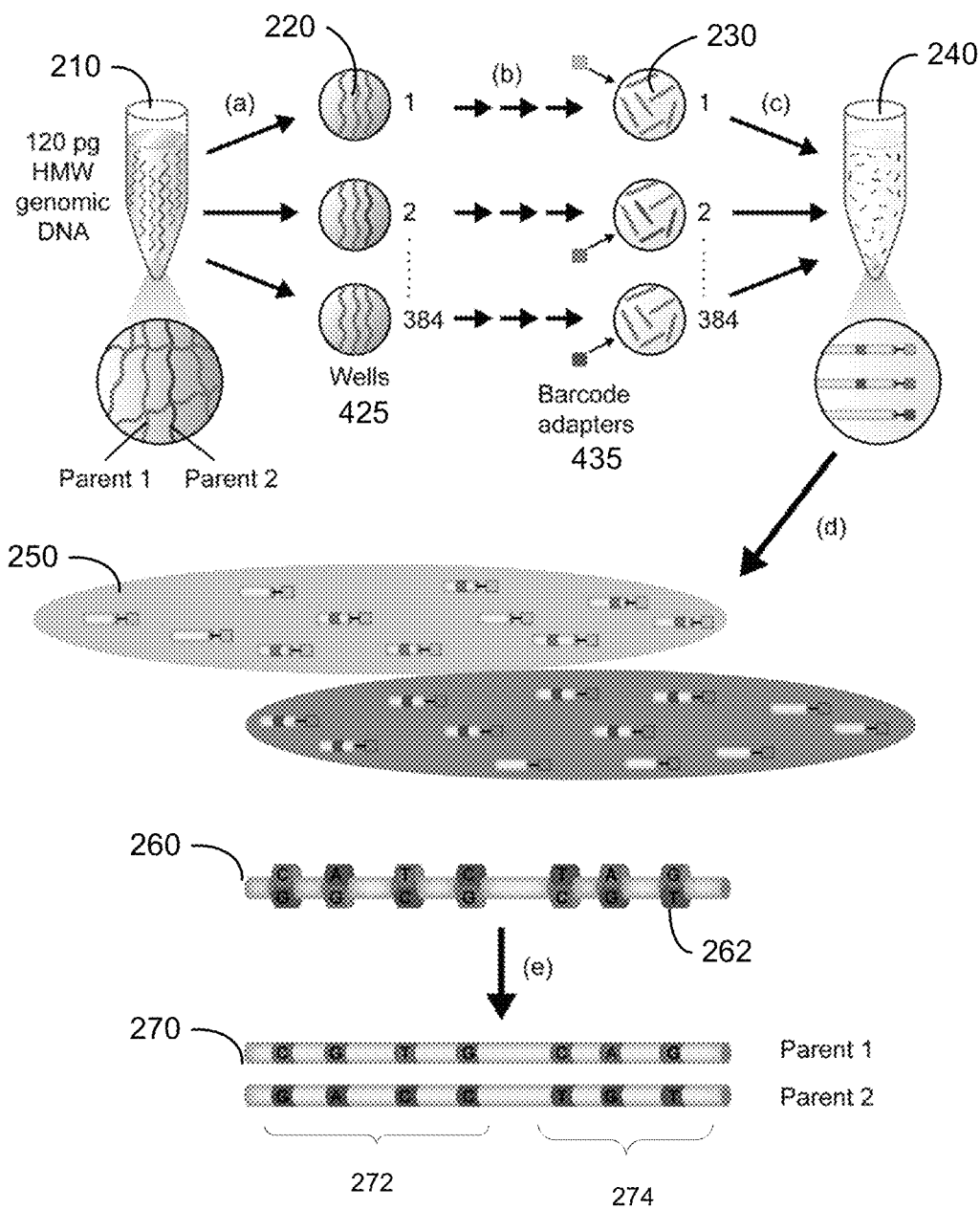
FIG. 2 shows a diagram illustrating steps of method 100 according to embodiments of the present invention.

In step 110, a solution including one or more samples of nucleic acid molecules of an organism is obtained. A sample itself can be a solution. The solution can be created from tissue samples, or samples obtained from a bodily fluid, such as blood. As shown in FIG. 2, sample 210 has approximately 120 pg of high molecular weight DNA. The DNA inherited from each parent is highlighted in blue (parent 1) and red (parent 2). In the solution, the nucleic acid molecules tend to be much longer than after the solution is dispensed (e.g. from a pipette) as an aliquot into wells for preparation for sequencing. These very long fragments in the sample 210 can be about 100 kb to 1 mb in length.

In step 120, the solution is distributed into physically distinct pools (e.g. wells). FIG. 2 shows in (a) the DNA being physically separated into 384 distinct wells 220. The separation can be a stochastic separation of corresponding parental DNA fragments into the physically distinct pools. The act of dispensing typically breaks up the nucleic acid molecules, e.g., as they move through the tip of the pipette. The nucleic acid molecules before dispensing are termed very long fragments, and the nucleic acid molecules after dispensing are termed long fragments. The long fragments in a well (or other container holding a single aliquot) may be about 5 Kb to 50 Kb in length (or up to a few 100s of Kb or even longer).

In one embodiment, the solution 210 can be relatively diluted with respect to the DNA (e.g. as few as about 10 to 30 cells may be in the solution). This dilution can provide an aliquot containing around 10% (or less, such as 1% or 0.1%; or higher, such as 20% or 30%) of the genome when the solution is dispensed from a pipette. As the fraction of the genome in each pool decreases to less than a haploid genome, the statistical likelihood of having a corresponding fragment from both parental chromosomes in the same pool decreases. For example, at 0.1 genome equivalents per well, there is a ten percent chance that two fragments will overlap and a fifty percent chance those fragments will be derived from separate parental chromosomes; yielding a five percent overall chance that a particular well will be uninformative for a given fragment. Thus, given that the long fragments are randomly distributed throughout the solution, the original fragments of an aliquot are not likely to be from overlapping regions of the genome, nor be close to each other, and to be from different copies of a chromosome.

These long fragments can be amplified (cloned). For example, a highly uniform amplification using a modified phi29-based multiple displacement amplification (MDA) (Dean, F. B. et al. 2002, PNAS Vol. 99, pp. 5261-6) was performed to increase the number of each long fragment of DNA to 5,000-10,000 copies per well. Amplification can help to provide better statistical data for coverage histograms, e.g., to determine pulses. The long fragments are not be cloned at all, or may be cloned in later steps.

In step 130, small fragments are generated from the long fragments. FIG. 2 shows the long fragments 225 being broken into small fragments 230 as shown in (b). The long fragments can be fragmented, e.g., using enzymatic fragmentation, multiple displacement amplification (MDA) with random primers, and/or physically fragmented (e.g. using sonic fragmentation). Short fragments result from the fragmentation of the long fragments. As part of an enzymatic process or as an additional step, the resulting short fragments may be amplified. In various embodiments, the resulting short fragments can be about 100-10,000 bases, or a more narrow range of 200 bases to 5,000 bases, and may be 500 bases on average.

As part of the fragmentation into small fragments, the long DNA molecules can be processed to blunt ended 300-1,500 by fragments through controlled random enzymatic fragmenting (CoRE). CoRE fragments DNA through removal of uridine bases, incorporated at a predefined frequency during MDA, by uracil DNA glycosylase and endonuclease IV. Nick translation from the resulting single-base gaps with *E. coli* polymerase 1 can resolve the fragments and generate blunt ends.

In step 140, well-specific barcode adapters (example of a label) are added to the small fragments. Thus, the short fragments of a single aliquot can be coded, as described in U.S. patent application Ser. No. 12/816,365 (which is incorporated by reference), to track the short fragments from a same well, when the short fragments from all wells are pooled into a single sequencing procedure. FIG. 2 shows barcode adapters 235 being added to the small fragments 230. Each well has a barcode that is unique to that well. In one embodiment, unique 10-base error correcting barcode adapters, designed to reduce any bias caused by differences in the sequence and concentration of each barcode, are ligated to the fragmented DNA in each well using a high yield, low chimera formation protocol (e.g., as described in U.S. application Ser. No. 12/697,995 and Drmanac, R. et al. 2010, Science, Vol. 327, pp. 78-81). In one implementation in step (b), the genomic DNA is amplified, fragmented, and ligated to unique barcode adapters, all within the same well without intervening purifications.

In step 150, the small fragments from the wells are combined into a single sequencing procedure to provide one or more sequences (e.g. mated arm reads). In FIG. 2 at (c), the fragments from all 384 wells are combined into a single vessel 240, with the barcode adapters 235 distinguishing the origin of each small fragment. Any sequencing platform can be used to obtain an entire sequence of a small fragment, one arm read, or a pair of mated reads. In one embodiment, an unsaturated polymerase chain reaction using primers common to the ligated adapters can be employed to generate sufficient template for sequencing [Drmanac, R. et al. 2010]. The small fragments can also be purified before the sequencing process begins. Alternatively, one could sequence each well in a separate process, but this can be time consuming.

The more individual pools interrogated the greater number of times a fragment from the maternal and paternal complements will be analyzed in separate pools. For example, a 384 well plate with 0.1 genome equivalents in each well results in a theoretical 19x coverage of both the maternal and paternal alleles.

In step 160, the sequences are mapped (aligned) to a reference genome and grouped by the barcode (i.e. by well ID). FIG. 2 shows group 250 of the sequences obtained from fragments from well 1, while the other group is of sequences obtained from fragments from well 2. The well ID (label) can be tracked and used for phasing and linking, where further details on linking are described below.

In one embodiment, one or more long fragments (pulses) can be determined for each well. The determination of the long fragments can be performed as part of phasing, and then the long fragments can be used later for linking. In one implementation, a histogram can be determined from the genomic coverage of each group. The pulses can be determined from non-zero or relatively high regions of the histograms (such regions may be contiguous or nearly contiguous with small gaps). As each group corresponds to long fragments that are likely not to be overlapping, the pulses can be determined to correspond to the long fragments 220. Accordingly, certain embodiments can track the aliquot (or well) from which a sequenced fragment was obtained, thereby recapturing information about the longer fragments that existed in the solution. This information about the longer fragments can provide more information about the respective chromosomes.

For example, when a low concentration sample is used, if arm reads from any two fragments in a same aliquot (well) are close in genomic location (as determined from the mapping), it can be assumed that they originated from a same original long fragment in the solution. Thus, the arm reads do not have to be of a same small fragment, but can be from any two fragments that are from the same aliquot. Such tracking provides more information about large regions on the chromosomes.

In step 170, the groups of aligned sequences can be phased (e.g. using the pulses) to obtain the two haploid genomes. Since pulses represent the boundaries of the long fragments, and each long fragment in sub-genome aliquoting such as LFR represents (with >95% confidence) a haploid genome, such a process can significantly simplify the task of DNA assembly. Ultimately, a high coverage complete sequence of both maternal and paternal chromosomes can be generated. FIG. 2 shows a diploid genome 260 of heterozygous loci 262 that is phased into the two haploid genomes 270 with the help of the knowledge of the labels.

The phasing can be done in various ways to determine which alleles corresponds to which haplotype. In one embodiment, a set of phased heterozygous loci (hets) can be referred to as a contig. For example, the hets of region 272 can be phased to determine a contig. And, the hets of region 274 can be phased to determine a contig. Thus, the result of the phasing can be a plurality of contigs. In another embodiment, pulses determined from each aliquot (or otherwise having a same label) can be phased, where a het may only have a phased pulse corresponding to only one haplotype.

It may not be known which haplotype of the first contig 272 corresponds to which haplotype of the other contig 274. Identifying which haplotype of which contig corresponds to a haplotype of another contig can be performed using universal phasing. This universal phasing can identify all the first alleles corresponding to the first parent and all of the second alleles that correspond to the second parent. Note that the two haploid genomes 270 show the result of universal phasing to match the haplotypes of each contig, thereby resulting in the phased hets of each contig being identified as parent 2 or parent 2. Further phasing can phase the contig in 270 with another contig to match up two haplotypes of the two contigs to be from the same parent. Additional information about phasing can be found in U.S. patent application Ser. Nos. 13/649,966, 13/591,723, and 13/591,741.

The use of labels to determine long fragment reads (LFR) can effectively perform sequencing of very long single DNA molecules, making assembly of separate haplotypes possible [Peters, B. A. et al. Accurate whole-genome sequencing and haplotyping from 10 to 20 human cells. *Nature* 487, 190-195 (2012)] with short sequence reads. In general, phasing rates were very high, with 1.65M-2.16M heterozygous SNPs in each genome located within haplotype contigs of N50 lengths 360 kb-590 kb. These results compared very favorably with previous LFR libraries made from ~150 pg of DNA (Table 300 of FIG. 3).

In determining table 300, all libraries were assembled to the NCBI build 37 of the human reference genome. High quality calls are based on certain quality metrics as further defined in Carnevali et al [Carnevali, P. et al. Computational Techniques for Human Genome Resequencing Using Mated Gapped Reads. *Journal of Computational Biology* 19 (2011)]. Candidate variants were phased using GenPhase [Peters, B. A. et al. 2012] with modifications, e.g., as described herein. For replicate LFR libraries from embryo #8, candidate variants from both replicates were used for phasing by each individual replicate. N50 calculations are based on the total assembled length of all contigs to the NCBI build 37 human reference genome. As marked by symbol †, the unamplified control genome of European decent was processed using from 5 ug of genomic DNA collected from an anonymous donor. As marked by symbol *, these libraries were made from high molecular weight DNA and have both an LFR and STD library. They were previously reported in Peters et al. 2012 and used here to demonstrate how many SNVs might be expected to be phased if material is not limiting. NA12892 was assembled using Complete Genomics' pipeline version 1.5 and NA19420 was assembled using version 1.8.

B. Other Labels

Another example of a label can be found in U.S. application Ser. No. 14/205,145, where a same label can be affixed to different segments of a same long fragment. If the long fragment is broken up into smaller fragments, each small fragment can include the same label. In other embodiments, different segments of the same long fragment can have a same prefix for the label, but have a different suffix. In this manner, a label can identify two small fragments as originating from the same long fragment. In one embodiment, a different label can be assigned as a tag to each long fragment, which can result in many (e.g., millions or billions) of tags, depending on the number of long fragments.

In another embodiment, the nucleic acids in each aliquot can be sequenced separately. In this manner, all the sequence reads obtained in a particular sequencing operation can be associated with the same label. This label can be assigned to the reads when the reads are stored as a group.

C. Expected Number

In various embodiments, an expected number of wells can be used to determine a threshold for linking a locus to one or more hets. For example, if 20 cells are used, then there should be about 40 fragments that correspond to a genomic location in the human genome (i.e., where the location is the same between both chromosomes). When the fragments are sequenced, this information can be conveyed in the labels, and used in the assembly process. Thus, one may expect about 40 different labels (e.g., +/−10) for reads that align to a contig at a particular position.

In addition to an expected number of labels, an expected number of reads can also be used. The expected number of sequence reads can be derived from the general genome coverage. For instance, if the coverage is 40× on average, one would expect around 20× to 60× reads for a healthy locus based on a statistical distribution. Genomic coverage (e.g., 40×) relates to the amount of sequencing done at the size of the genome. For human genome, 40× multiplied by $3*10^9$=120 billion bases sequenced.

The genomic coverage can be mandated by the required accuracy and tolerable cost. If the required accuracy is 60× and there are only 10 cells, then that dictates a minimum amount of amplification that is needed. Thus, the amount of amplification can be dictated by the sequencing depth desired and the number of initial cells. The amount of coverage after amplification is much higher than that actually performed. For instance, there may be enough amplicons to obtain 1000× after amplification, but only a portion of the amplicons may be sequenced, e.g., the amplicons may be sequenced to achieve 40× coverage.

II. LINKING

The phasing of hets to determine contigs can provide information about what alleles are on the same chromosome copy. However, these phased hets do not provide information about what is between the hets. The genome is not simply identical to the reference genome in between the phased hets, as some loci may be ambiguous, not sequenced, or difficult to categorize. Embodiments are directed to resolving one or more bases calls at genomic positions linked to hets. Such genomic positions may include certain types of variations relative to a reference genome.

Variations that may need resolving include insertions, deletions, and block substitutions. These variations can be difficult to map to a reference, and thus a relatively low number of reads may correspond to such variations. Thus, it is difficult to know whether or not there is an error in the sequence read or if there is actually an indel (insertion or deletion). The difficulty increases for large indels, particularly due to the variability in length.

One might try to include such variations in the phasing process, thereby having an allele of a het be one of these variations. But, a relatively high error rate for these variations can cause inaccuracies in the phasing process, thereby leading to even more errors (e.g., 10 times the error rate for SNPs). Further, if one puts more relaxation (e.g., allowing gaps in reads or reference, and allowing mismatches) into the parameters to allow aligning to indels can cause mapping to no longer be unique anymore. Thus, the flexibility can cause a sequence read to map to multiple places in the reference genome.

A. Linking with Shared Labels

Figure 4:
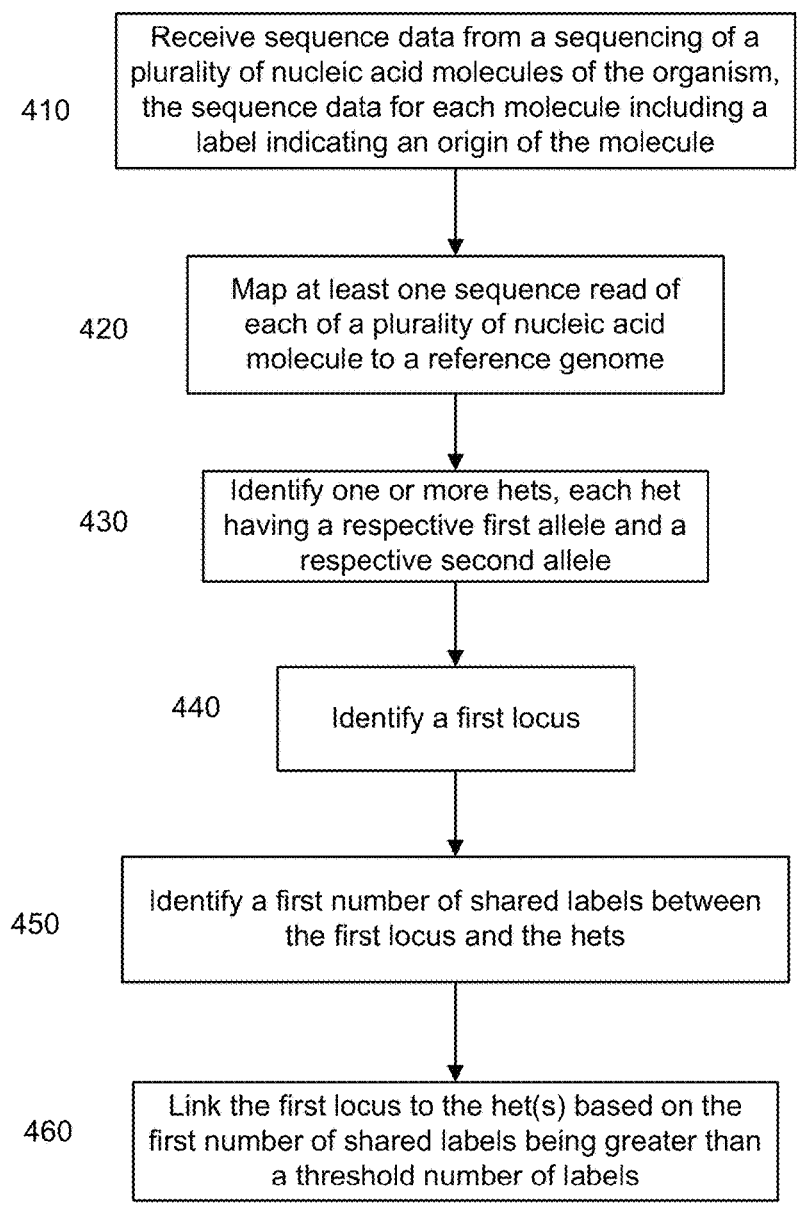
FIG. 4 is a flowchart of a method 400 for linking a first locus to one or more hets according to embodiments of the present invention.

As mentioned above, problems can occur in phasing due to sequencing errors at certain loci. Embodiments can identify such problematic loci and not use them for phasing. After phasing, these problematic loci exhibiting base calls different from the reference genome can be subjected to further analysis (e.g., involving linking) to determine the correct bases at these problematic loci for each haplotype of a contig. Embodiments for linking are now described FIG. 4 is a flowchart of a method 400 for linking a first locus to one or more hets according to embodiments of the present invention. Method 400 may be performed entirely or partially by a computer system, as can other methods described herein.

At block 410, sequence data is received from a sequencing of a plurality of nucleic acid molecules of the organism. The nucleic acid molecules can correspond to small fragments as described herein. The sequencing of a nucleic acid molecule may be performed using any suitable sequencing technique. The sequence data for each of the plurality of nucleic acid molecule can include one or more sequence reads of at least one portion of the nucleic acid molecule. For example, the sequence data can include mated reads of a mate pair, or just be a single sequence read.

The sequence data can also include a label corresponding to the one or more sequence reads. A single label can correspond to all the sequence reads for a given molecule. A label can be stored for each sequence read, or stored once for all reads of a given nucleic acid molecule. As described above, the label indicates an origin of the nucleic acid molecule, e.g., the origin being a well or specific long fragment which the molecule originated. A same label on two nucleic acid molecules indicates a same origin for the two nucleic acid molecules (e.g., a same well or a same long fragment).

At block 420, for each of the plurality of nucleic acid molecules that are sequenced, at least one sequence read of the nucleic acid molecule is mapped to a reference genome. The mapping may be done in a variety of ways and using various criteria. For example, a mapping may allow or not allow mismatches between the sequence read and the reference genome. The mapping can use k-mer indexes for the reads and for the reference. Matching k-mers can indicate a possible alignment.

Once a read is mapped, the base calls of the read can be tracked for the genomic positions to which the read mapped. In this manner, the number of various base calls of reads that align to a particular genomic position can be tracked, along with the various labels of each read.

At block 430, one or more hets are identified. Each het has a respective first allele and a respective second allele. Each of the hets may be identified based on an sufficient indication of the two different alleles. For example, a certain number of reads or labels (i.e., unique labels of reads aligned to the het) having each of the two alleles can be required, as well as any other allele having less than a specified number of reads or labels. When there are multiple hets, the hets may be phased to obtain a contig.

At block 440, a first locus is identified. The first locus may be a single genomic position or region that includes a plurality of genomic positions, which may or may not be contiguous. The first locus may be identified because the first genomic position of the first locus has ambiguous base calls. For example, the number of reads aligning to the first locus may be relatively low. As another example, three different base calls may be identified on reads aligning to the first genomic position. The first locus would not be one of the hets.

At block 450, a first number of shared labels is identified. The shared labels are between the first locus and the het(s). For example, reads having labels {25, 56, 95, 112} may align to the first locus and be considered a first set of labels. And, reads having labels {25, 56, 95, 156, 178} may align to any one of the hets and be considered a second set of labels. Thus, even if a read only aligned to one of the hets, the corresponding label would be included in the second set of labels. In this example, the shared labels are {25, 56, 95}. Accordingly, each shared label corresponds to one or more sequence reads mapping to the first locus and corresponds to at least one sequence read mapped to at least one het.

At block 460, the first locus is linked to the het(s) based on the first number of shared labels being greater than a threshold number of labels. In one embodiment, the first locus can always be linked to the het(s) when the first number is greater than a threshold number. In other embodiments, other criteria can be required in addition to the first number being greater than a threshold number. For example, a het can be required to be within a specified distance of the first locus.

Once the first locus is linked to the het(s), the shared labels and the corresponding reads can be analyzed. This analysis can allow for the detection of indels, block substitutions, and changes from a no-call on one haplotype to an actual base call. Such applications are described in more detail below. A particular embodiment for linking is described in the next section.

In some embodiments, a locus can be linked to more than one het, and more than one het can be used to determine whether a locus is linked to any of the hets of a contig. In such cases, a minimum number of hets (e.g., an absolute number or a percentage) can be required to share a label before the label is considered a shared label. For example, if the minimum number of hets is two, then label 25 is considered a shared label only if label 25 appears for at least two hets. This can reduce false positives in the identification of shared wells. Too large of a number might cause false negatives, and thus an appropriate threshold can take into account false positives and false negatives. The number of shared labels can then be used as a criterion as whether the locus is linked to any one het or to a contig of a plurality of hets. In one embodiment, all hets of a contig can be linked if the number of shared labels is above the threshold. In this manner, an accuracy can be increased as to whether the locus is linked to a contig.

In another embodiment, a counter can be incremented for each label shared with another het. Thus, if a label is shared with more hets, then the counter is higher. This counter can be used as a weighting factor. This allows for weighting a read that has support from multiple hets higher than a read that has support for just one het.

B. Linking Using Window

As mentioned above, the first locus can be linked to a plurality of hets. Prior to linking, these hets can be phased to obtain a contig. Thus, the first locus can be linked to the contig.

Figure 5:
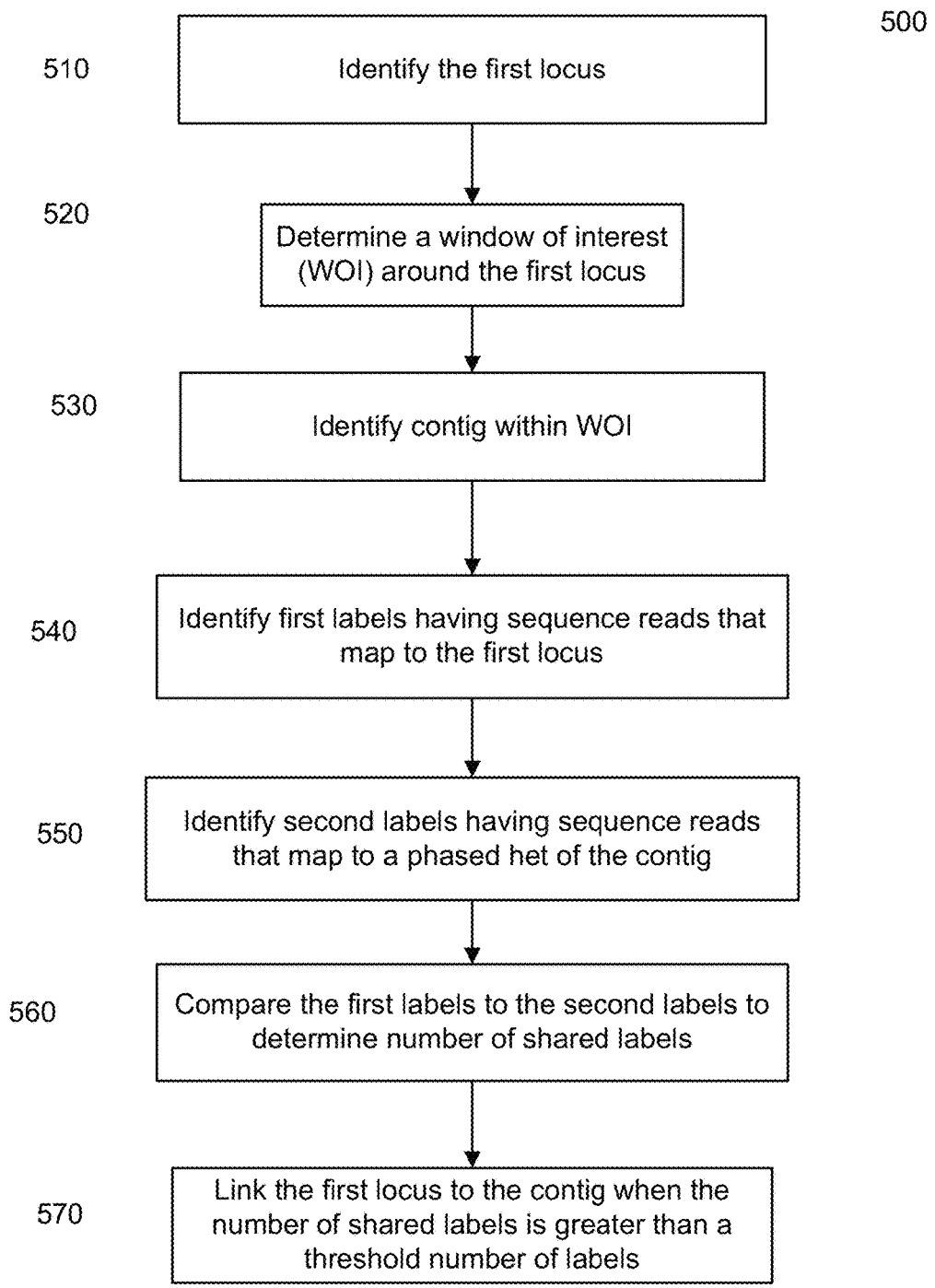
FIG. 5 is a flowchart of a method 500 for linking a first locus to a contig according to embodiments of the present invention.

FIG. 5 is a flowchart of a method 500 for linking a first locus to a contig according to embodiments of the present invention. The first locus can be homozygous or heterozygous, i.e., the sequence reads mapping to the first locus can show just one base or multiple bases. Accordingly, heterozygous and homozygous loci can be linked. The first locus can also be called a locus of interest (LOI). Other embodiments may employ other techniques for linking a locus to a phased het.

Method 500 can be performed after the phasing process that provides a plurality of contigs. In one embodiment, there is at most one contig determined for any position in the genome. In other embodiments, more than one contig can be determined for any genomic position.

At block 510, the first locus is identified. As mentioned above, the first locus can correspond to an ambiguous locus, which may have low coverage or contradictory base calls. Various criteria can be used, e.g., as described herein.

At block 520, a window of interest (WOI) around the first locus is determined. The extent of the WOI can be related to the expected size of the long fragments (e.g., 20-100 Kb). For example, the WOI can be taken to have the width of the maximum allowed pairing distance between two arm reads (e.g., 10 Kb). That is, plus or minus 50% (0.5 multiplied by the maximum) on each side of the locus, which is a fraction of the expected fragment size (e.g., 20-100 Kb). The WOI can have just one het identified.

At block 530, a contig within the WOI is identified. In one implementation, as long as a contig includes just one genomic position within the WOI, then the contig can be considered to be within the WOI. In another implementation, a specified number of genomic positions of the contig may be required to be within the WOI.

In an embodiment where there is only one contig per genomic position, method 500 can identify the contig at either end of the WOI. In some cases, a contig could be smaller than a WOI, thereby having more than just two contigs. The longest contig of the contig within the WOI can be chosen as the identified contig.

The identified contig can be chosen based on other criteria besides or in addition to length, e.g., to determine a reliability score for a contig. For example, a criterion can involve the sum of the strength of connections (e.g., as used in the phasing step) between hets of the contig. The sum can be used as a measure of reliability. The connections can be just between hets in the WOI or for the whole contig. An example of another measure is the het density in the regions of interest for the contig or the whole contig. In one implementation, the contig with a largest reliability score can be selected.

In one embodiment, if the contig is within the WOI, then the first locus can be linked to the contig, and method 500 can stop. In another embodiment, further criteria is used to determine whether the first locus is to be linked to the contig.

At block 540, first labels (e.g., wells IDs) having sequence reads that map to the first locus are identified. The sequence reads can be mapped to a reference genome to identify the sequence reads that map to the first locus. The labels of these mapped reads can then be identified as being first labels corresponding to the first locus. The number of reads that map to the first locus may be more than the number of first labels, as more than one read from an aliquot may map to the first locus.

At block 550, second labels having sequence reads that map to a phased het of the contig are identified. The second labels can correspond to any read that maps to at least one of the hets of the identified contig. The second labels can correspond to reads from either of the two phased haplotypes. In this manner, information for just one haplotype can be obtained, if that is all that is available.

At block 560, the first labels are compared to the second labels to determine the number of labels shared between the first labels and the second labels. The shared labels provides an indication that a sequence read for the first locus was on a same long fragment as a sequence read for at least one of the phased hets of the contig. As will be described later, such information can help resolve base calls and identify hemizygous deletions.

At block 570, the first locus is linked to the contig when the number of shared aliquots is greater than a threshold number of labels. For example, if the overlap between the two sets of labels (i.e., first labels second labels) was more than the allowed threshold (e.g., 2, 3, 4, or 5), the first locus may be declared as linked to the identified contig. The threshold can be a dynamic value that is dependent on the current sample and other parameters, for example, how many cells were used, the number of possible labels (e.g., number of aliquots), as well as the amount of genomic DNA in each aliquot, the amount of amplification per aliquot, and how much sequencing was performed (e.g., sequencing coverage and/or depth). In various embodiments, the threshold number can be a ratio or percentage of total labels (e.g., dependent on the sequencing depth, where more sequencing depth required more labels) or an absolute number.

The threshold number of labels can differ depending on properties of the first locus. For example, if the first locus is heterozygous, the threshold may be similar to those used in a pairing process of phasing [Peters, B. A. et al, Nature (2012)]. As another example, if the first locus is homozygous, the threshold may be simplified, e.g., the only requirement being that the number of shared labels is greater than the threshold number (e.g., 1, which is the same as equal to 2).

Once a region is linked to a contig or het(s), the sequence reads of a label can be associated with a particular haplotype, even if the locus is homozygous. For example, the reads of the first locus might only share labels (or many more labels) with only one haplotype. Various embodiments can use the linking of the first locus to a het to improve the determination of the genome between hets.

III. IMPROVING BASE CALLS USING LINKING

The locus being linked typically has ambiguous base calls, which can cause errors or no-calls (which have a negative impact of gaps in a genome). If phasing is done first to obtain contigs of good quality, these ambiguous loci can be linked to the contigs. Then, the reads and the corresponding labels can be analyzed to resolve base calls. Since reads having the same label are evidence of the reads being on a same long fragment, this additional information can help resolve seemingly inconsistent data.

A. Method

Figure 6:
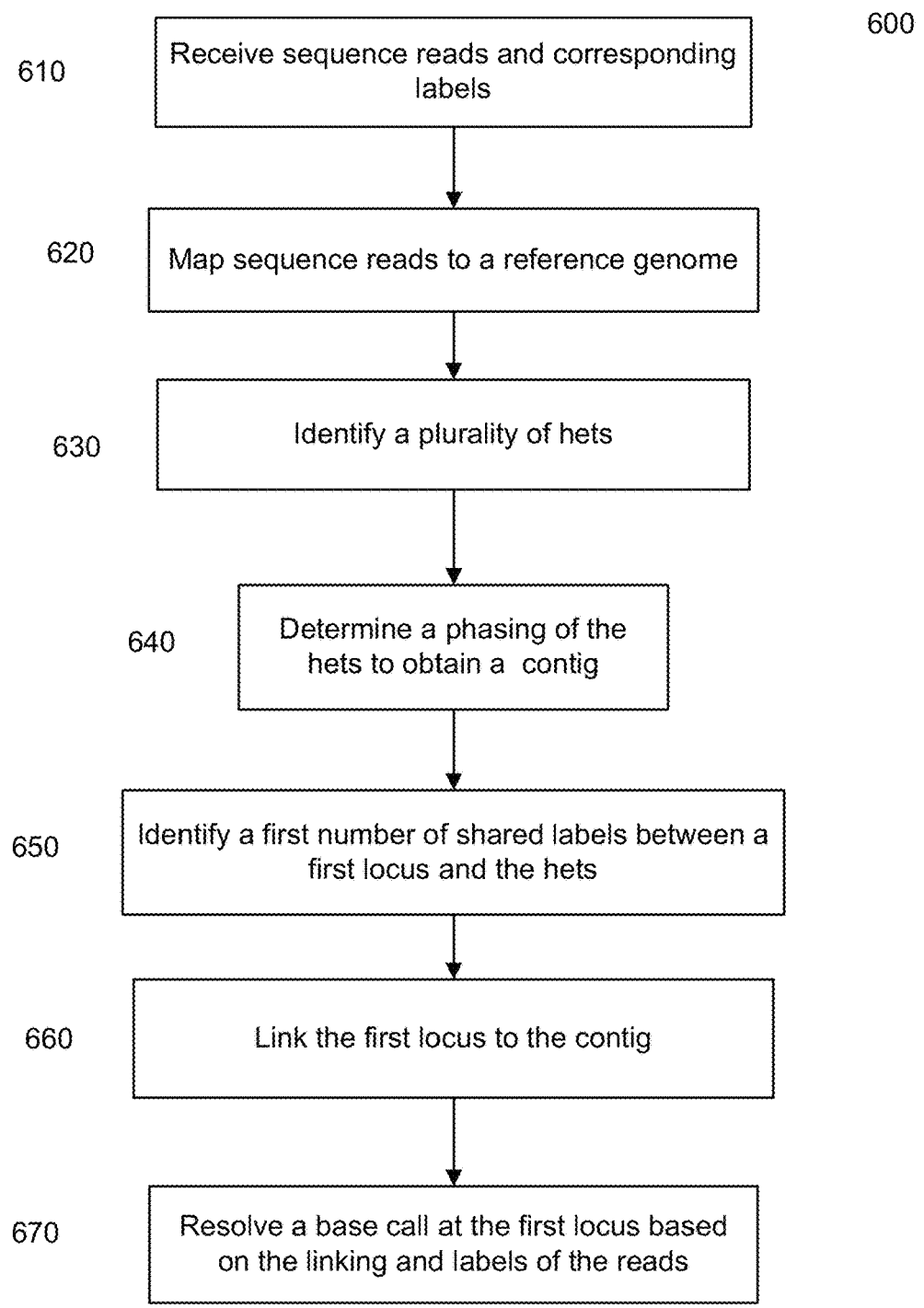
FIG. 6 is a flowchart of a method 600 of determining a haplotype of an organism from a sample obtained from the organism according to embodiments of the present invention.

FIG. 6 is a flowchart of a method 600 of determining a haplotype of an organism from a sample obtained from the organism according to embodiments of the present invention. Method 600 can use linking of a first locus to a contig of the plurality of hets to resolve base calls on one or more haplotypes of the organism.

At block 610, sequence reads and corresponding labels are received. Block 610 can be performed in a same manner as block 410 of method 400. The sequence data for each of the plurality of nucleic acid molecule can include one or more sequence reads and a corresponding label corresponding to the one or more sequence reads.

At block 620, the sequence reads are mapped to a reference genome. For example, a computer system can map at least one sequence read of a nucleic acid molecule to a reference genome. Block 620 can be performed in a same manner as block 420.

At block 630, a plurality of hets is identified. Each het has a respective first allele and a respective second allele. Each of the hets may be identified based on a sufficient indication of the two different alleles, e.g., as described herein. The hets also may be identified based on a strong connection to other hets, where such a connection can be used for phasing. U.S. patent application Ser. Nos. 13/591,723 and 13/591,741 provide details on determining connection strengths between hets.

At block 640, a phasing of the first and second alleles of the hets is determined. The phasing can be used to determine a contig that specifies the first alleles as corresponding to a first haplotype and the second alleles as corresponding to a second haplotype. Phasing can be determined via calculation or simply read from memory.

Various techniques can be used for phasing. For example, the labels of the reads mapping to the hets can be used to determine which alleles corresponds to which haplotype. In one embodiment, the phasing can be performed using a graph of the hets, where the selected phasing corresponds to a minimum spanning tree of the graph, as determined using connection strengths between pairs of hets. U.S. patent application Ser. Nos. 13/591,723 and 13/591,741 provide details on techniques that can be used for phasing.

At block 650, a first number of shared labels is identified. The shared labels are between a first locus and the hets. The first locus can be selected based on various criteria, e.g., as mentioned herein. The first locus would not be one of the plurality of hets.

In one embodiment, the shared labels can be determined from a first set of labels that corresponds to reads aligning to the first locus and from a second set of labels that corresponds to reads aligned to any one of the hets. The overlap between the two sets can correspond to a set of shared labels. In another embodiment, the shared labels can be identified by examining whether each potential label is shared by reads that align the first locus and reads that align to any one of the hets. Regardless of the technique used, each shared label would correspond to one or more sequence reads mapping to a first locus and corresponds to at least one sequence read mapped to at least one het of the first contig.

At block 660, the first locus is linked to the first contig. Whether the first locus is linked to the first locus can be based on shared labels among reads at the locus and the first hets of the first contig. For example, the first locus can be linked based on the first number of shared labels among the first locus and any one of the first hets being greater than a threshold number of labels. In another embodiment, the number of hets with shared labels can also be used in addition to or instead of the criteria of the number of shared labels. For example, at least two first hets can be required to share a label with a read at the first locus.

At block 670, a first base is resolved to be at the first locus for the first haplotype. Thus, the first haplotype can be determined to have the first base at a first genomic position of the first locus. The resolving can be based on the first base being at the first genomic position on locus sequence reads (i.e., reads at the first locus) that each shares a label with at least one het sequence read (i.e., a read at one of the first hets) including a first allele of the first haplotype. Thus, the shared labels are with a particular haplotype. The number of hets with shared labels can be required to be greater than a minimum value (e.g., greater than one). Thus, the het sequence reads can cover at least two of the first hets.

As an example of resolving, sequence reads that have a first base at the first genomic position can consistently have the same label as sequence reads that have one or more first alleles at the hets for the first haplotype. In this manner, the first base can be determined to correspond to the first haplotype. Thus, the first base can be resolved based on the first base being at the first genomic position on sequence reads that have a same label as sequence reads including at least one first allele of the first haplotype. A second base for the second haplotype may or may not be resolved.

As described in more detail below, the linking can use the plurality of hets in a variety of ways. For example, a requirement of having at least two hets (or some other minimum number) share a label with a read from the first locus can decrease false positives and remove reads that might be faulty. In such an embodiment, the resolving may only use locus sequence reads that share a label with het sequence reads from at least the minimum number of hets.

Alternatively or additionally, by counting each of the hets with a shared label, base calls corresponding to labels shared with more hets are weighted higher. In this embodiment, a sum of counts of shared labels across the first hets can be calculated for a plurality of base calls at the first locus. A sum can be calculated for each haplotype, thereby potentially providing a table that is of size 2×4, for the two haplotypes and each of the four bases.

B. Phasing

As mentioned above, the hets that are phased to obtain the contig may be specifically chosen to be high-quality hets to provide accurate phasing. This selection of high quality hets can help to reduce errors that may result in an allele being associated with the wrong haplotype or just an incorrect allele from being identified. Thus, embodiments can throw away hets (e.g., instances where an allele is an indel or low quality SNPs) where there is not good confidence, and not use them for phasing. However, these low confidence hets can be used at a later time in a linking process to resolve the base calls at such a locus.

Using low-quality hets can result in a graph that is sub-optimized due to low-quality hets that inadvertently cause a wrong path to be selected (i.e., an incorrect phasing). The low-quality hets can also cause short contigs, in addition to a high probability of switching error in phasing.

A low-quality het (e.g., a SNP) can be characterized as exhibiting inconsistent data, which can show up as a low connection strength between the low-quality SNP and another SNP. For example, one allele of the low-quality SNP can share labels with two alleles of another SNP, which would be inconsistent if the low-quality SNP also had reads for a second allele. Also, there can only be a few reads mapped to a low-quality SNP, thereby causing a low confidence. Having only a few reads can be caused by an indel.

In some embodiments, a low-quality het can be identified using a connectivity matrix. In other embodiments, a connectivity matrix is not needed. A connectivity matrix can be used later for performing corrective action, as described herein.

FIG. 7A shows a connectivity matrix 700 having inconsistent data. The rows and columns correspond to the four different bases for two different genomic positions. The values in the matrix cells correspond to a consistency in the reads with the selected alleles having a same label. In various embodiments, the specific value of a cell can correspond to a number of unique labels, the raw value of the number of reads having the same label, or the sum of the lowest number of consistent reads from each label (e.g., if C shows up at position #1 three times for label #1, and C shows up at position #2 two times for aliquot #1, then the value of two is added to the {C,A} matrix element).

As shown, position #1 appears to show C being on both haplotypes since it has labels that correspond to A and C on positions #2. This could be the result of position #1 being homozygous for C, but then there are also reads with G having a same label as the C allele for position #2. It can be determined which position is of low-quality by looking at other connectivity matrices for the two different positions, e.g., relative to a position #3 and so on.

FIG. 7B shows a connectivity matrix 750 having a low number of reads. A different connectivity matrix for position #1 or position #2 can have more values, since the low-quality position (which may be #1 or #2) can cause the low numbers for this particular connectivity matrix. After linking, more reads can be available since the linking can be done to a whole contig as opposed to just one SNP.

The inconsistent data or the low number of mapped reads can be the result of read errors. The result of the inconsistent reads can lead to a no-call at a position or an incorrect base call (e.g., homozygous when heterozygous is correct, or vice versa). But, one can recover some of those using the linking process.

The problem can be more pronounced for indels. For SNPs, there is only four by four matrix that contains all the combinations. For insertions and deletions, if you want to look at the whole space, it is effectively infinite. A single cell can be used to identify another category (e.g., "O" for other), but this lumps all other possibilities together, thereby making the analysis less accurate. Thus, it is difficult to phase indels. And, the lumping of other possibilities together can be required for SNPs when connecting an indel to a SNP.

A downside of using less hets is that less coverage of the genome is determined for the contig. Thus, techniques typically use any locus that appears to be a het, even indels and loci with ambiguous data. But, as described above, errors can ensue. Embodiments can overcome both problems (i.e., coverage and errors) by using linking to fill in the gaps left by not including such low-quality hets in the phasing process. Thus, all the potential hets are ultimately used in determining the final contig.

Accordingly, the linking process allows one to split the task of phasing to have the best of both worlds. The use of high quality SNPs means that yield (coverage) is compromised, but an accurate contig is obtained. And, then linking is used to bring back the yield. Further, if a mistake is made in linking, the error doesn't propagate as further assembly of contigs is not dependent on the linking of the one locus. In this manner, a strong backbone is obtained that can be linked to, as opposed to having a broader backbone that is weaker. And, the probability of that making a switching error where everything after that point is wrong is reduced.

In various embodiments, high quality SNPs can be identified using connection strengths between two SNPs and based on the quality scores of the base calls for reads mapping to the SNP. A quality of a base call can be dependent on signals obtained as part of the sequencing process, the mapping of sequence reads to the first hets (e.g., whether the read was a perfect match to the position, or whether there was one or more mismatches), and an assembly of sequence reads covering the SNP (e.g., the various bases of the reads mapping to the position).

Besides phasing to create a contig, contigs can be phased to determine which contigs are on a same haplotype. After the universal phasing, a universal linking step can be performed. The universal linking can be used to identify more shared labels as more hets can be used (i.e., all hets from the contigs identified as being on the same haplotype). For example, contigs on both sides of the locus can be linked to. This can allow more loci to be linked (e.g., to satisfy a threshold), and more reads can be analyzed (due to more hets) to help resolve base calls.

C. Identifying No-Calls

A no-call at a particular position indicates that not enough data is available to make an accurate determination, or there is inconsistent data. A no-call could be result of a deletion, a wrong base, or a low coverage region. The no-calls reduce the call rate for the genome. When there is a low number of reads, the position usually is a no call. For example, if there are five reads that support C, but the average expectation is 40×, then five can be considered too low.

Linking techniques can be used to resolve the ambiguity of the no-call. For example, one can identify a location that has C on both haplotypes (even though the number of reads is low) if reads with C show up for both haplotypes. But, if C only shows up for one haplotype, then the system can call C for one haplotype, and a no-call for the other haplotype. Even if one haplotype is called, it is better than both haplotypes not being called. This determination can be made in a final base calling, i.e., after a linking process.

The inaccuracies that cause no calls can result for various reasons. For example, one of the haplotypes may have just not been sequenced very much, or that one haplotype might include a deletion. Another reason is a lack of accuracy of an alignment algorithm, as the alignment might encourage particular base calls. Another reason is that a locus can be in a low coverage region, which can occur due to coverage bias (e.g., as a result of GC content). Thus, the haplotype with low coverage can have less than half of the reads as the other haplotype.

FIG. 8A shows a diagram 800 of a process of linking a locus 820 to multiple hets. Hets 810 and 830-850 show the alleles for the two haplotypes. The label 860 is shown on the right side of diagram 800. For each label, reads corresponding to the label are shown to the left at a location corresponding to the corresponding het or to locus 820. The horizontal line is shown for a read (e.g., for read 831) to indicate which haplotype the allele corresponds.

For label 3, only two reads are shown. The read for locus 820 is C, and the read for het 830 is C. In one embodiment, such a pair of reads with a shared label can result in label 3 being identified as a shared well with het 830. If only het 830 was linked and used to resolve the base call at locus 820, then locus 820 might result in a no-call for both haplotypes because there are only 4 reads. Also, the C on het 830 is linked to different base calls for locus 820 (e.g. label 3 and label 28 have different base calls for locus 820), and thus not even the C might be called to appear for haplotype #1. In another embodiment, label 3 would not be added as only one het is found to have the same label. In yet another embodiment, label 3 is only weighted with a 1, since only one het is found to share that label.

For label 11, reads exist for locus 820 with a C, het 830 with a C, and het 840 with T. Such reads are consistent since the reads for hets 830 and 840 are both from haplotype #1. Given that two hets have the shared label, such a read can be considered of higher reliability as to the actual base call on locus 820.

For label 28, reads exist for locus 820 with a G, het 830 with a C, and het 850 with a C. The reads on hets 830 and 840 are not consistent as both haplotypes are represented. Thus, the base call G at locus 820 is suspect, and potentially label 28 is not considered to be a shared label. If het 850 was not considered, then label 28 might otherwise have been considered a shared label, which might lead to errors. Accordingly, in one embodiment, the consistency of reads at the multiple hets is considered when resolving a base call, and in whether to consider the label a shared label.

For label 45, reads exist for locus 820 with a G and for het 840 with an A, which corresponds to haplotype #2. Depending on the embodiment, label 45 might (e.g., minimum number of hets not required) or might not (e.g., minimum number of hets greater than one is required) be considered a shared label.

For label 68, reads exist for locus 820 with a T, het 810 with a T, and het 830 with a G. Het 810 may be part of the same contig as hets 830-850, but could be a part of a different contig. Given that there are two hets that share label 68 with locus 820, the base call of T can be considered more reliable.

For label 93, reads exist for locus 820 with a T, het 810 with a T, and het 840 with an A. If only het 830 was used to link with locus 820, this shared label might be missed. In this manner, embodiments can use more data to resolve base calls at a locus.

FIG. 8B illustrates a process of using linking of a locus to multiple hets to change no-calls (N) to base calls according to embodiments of the present invention. The hets 810 and 830-850 and locus 820 are shown again. Below, each het is shown the connectivity matrix with locus 820. These connectivity matrices are summed to provide a total matrix for linking locus 820. In various embodiments, the total matrix can be a simple sum of the connectivity matrices (thus using weights) or of only the unique shared wells (i.e., a shared well is added only once).

To demonstrate the potential of embodiments to rescue no-call positions, three examples are shown where locus 820 would normally be a no-call if just the reads were analyzed and if only one of the connectivity matrices were analyzed.

Note that some of the shared labels for each connectivity matrix might be the same across hets.

In the examples shown, the distribution of shared wells (wells having at least one read for each of two bases in a pair) allows for the recalling of the base calls. Thus, these positions were able to be "recalled" due to the presence of shared wells between the neighbouring phased hets and the linked no-call position. Using well (label) information allows accurate calls of an allele with as few as 2-3 reads, if found in 2-3 expected wells, about three-fold less than without having label information. Thus, the number of no-calls can be reduced.

For example 1, the connectivity matrices for hets 830 and 840 show some inconsistencies, and just one shared well for het 810. If just these connectivity matrices were considered, then locus 820 might remain a no-call. But, the inconsistencies were different among hets 820 and 830, and when combined with the connectivity matrix for het 840 show a clear indication that locus 820 is a het with C for Hap 1 and G for Hap 2.

For example 2, the connectivity matrices for hets 810 and 830 have just one shared well, and the connectivity matrices for hets 840 and 850 show that the locus might be a het. However, when the matrices are summed, it is clear that Hap 1 has C at locus 82. Although Hap 2 would still be a no-call, the base call for Hap 1 has been resolved.

For example 3, locus 820 can be identified as having C for both haplotypes. Any one of the connectivity matrices either has low coverage, inconsistency, or is related to just one haplotype.

D. Variants

By using strong SNPs, false-positive SNPs do not corrupt the phasing process and cause errors in the contigs. In addition, the linking process can eliminate false-positive heterozygous SNVs or verify other calls (e.g., homozygous reference or homozygous variant). The linking can take advantage of the principle that errors incorporated during amplification, sequencing, and mapping in individual pools of DNA are unlikely to repeatedly occur exclusively on one parental chromosome. Thus, the reads that correspond to both haplotypes can be identified as errors when there is strong evidence of a heterozygous SNV.

By linking these SNVs to the surrounding heterozygous SNPs, one can assess whether the variant is in phase with one or both haplotypes. Those SNVs that are found to be in phase with both haplotypes (an impossibility for a heterozygous variant) are likely to be sequencing or mapping errors. Conversely, those variants that are in phase with a single haplotype, but are only found in one DNA pool are likely to be errors incorporated during the early amplification steps.

Four of the genomes analyzed in this study were preprocessed using LFR prior to being analyzed. Using replicate libraries from embryo #8, we can examine what improvements in SNV calling can be made through incorporation of haplotype information. Over 2M (98%) heterozygous SNPs shared between replicates 1 and 2 were phased, as shown in table 1.

TABLE 1

|  | Rep. 1 expanded | Rep. 2 expanded | Shared | % rep. 1 shared | % rep. 2 shared | Phasing rate |
|---|---|---|---|---|---|---|
| All heterozygous SNPs | 2,306,572 | 2,303,195 | 2,102,016 | 91.1 | 91.3 | — |
| Linked heterozygous SNPs | 2,154,462 | 2,096,663 | 2,060,896 | 95.7 | 98.3 | 98.0 |

Table 1 shows phased SNPs are highly shared between replicate libraries from embryo #8. The "expanded" label refers to SNPs called by a standard variant calling program or the LFR phasing program supplied with candidate variants for phasing from both embryo #8 libraries. The overall phasing rate is the number of SNPs shared and phased over the total number of shared SNPs. The replicate 2 biopsy has a partial hemizygous deletion of chromosome 13 resulting in 26,000 less heterozygous SNPs; this explains about half of the difference in phased SNPs between libraries. The remaining difference in SNPs is likely due to reduced genome representation in replicate 2 as a result of starting from 4 cells versus 10 cells. These two things explain the lower percent of replicate 1 shared for the phased heterozygous SNPs.

The high percentage of shared SNPs shows good repeatability. This demonstrates ~99% SNP phasing rate in each library for the shared SNPs and indicates a "phased discovery rate" of ~94% taking into account ~5-6% of heterozygous SNPs reproducibly not called in either library as indicated by the genome calling rates and by 2.1M shared SNPs as seen in previous high quality non-LFR libraries (Table 300).

1. Heterozygous SNVs

FIG. 9A is a matrix 900 illustrating the linking of the locus to the two haplotypes. As shared labels with any of the hets used to determine haplotype 1 or haplotype 2 can be used, the values can be increased relative to a connectivity matrix between two positions. In the example shown (cf. FIG. 7A), the counts are increased due to more reads having other shared labels. The evidence is now stronger that the locus is heterozygous for A and C.

In one embodiment, the matrix 900 can have a row "Other" that corresponds to an aliquot (or other label) having a sequence read at the linked locus, but where there is not a phased pulse (or read corresponding to a phased het) within a window of interest around the locus for the given label. The "Other" row could also correspond to reads where multiple haplotypes occur.

2. Homozygous SNVs

An advantage of linking is that one can link homozygotes (homozygous loci), which can be done with phasing. Accordingly, embodiments can "link" homozygous SNVs to contigs of phased heterozygous SNPs. This allows for the confirmation that a variant is present in both homologous chromosomes and the variant is not called homozygous due to allelic loss during MDA amplification.

FIG. 9B is a matrix 950 illustrating the linking of the locus to the two haplotypes. The evidence is now stronger that the locus is homozygous for C. If the reference has a different base than C, this locus would be identified as a homozygous SNV, as it is a variant relative to the reference.

To better understand how this can improve the error rate in homozygous SNVs, we can use the same replicate libraries from embryo #8. About 1M homozygous SNVs shared between replicates were linked, increasing the percent of shared homozygous SNPs in replicate 2 from 89.4% to 97%, as shown in table 2.

longer fragments can span the RLHs, and thus allow heterozygous from very far away to still be linked to a locus in an RLH.

E. Linking to Connect Contigs

After phasing to obtain a contig, there might be a point where the contig cannot be phased with a next het. At that point, a lower quality het can be used to link to the haplotypes of the contig. If this lower quality het is external to the contig (i.e., past an end of the contig), this lower quality het can be used to extend the contig (e.g., if sufficient, consistent data is available) and possibly be used to bridge between two contigs.

IV. IDENTIFYING HEMIZYGOUS DELETIONS

Linking can also be used to identify hemizygous deletions. A hemizygous deletion is when one haplotype has a region (e.g., just one base, non-contiguous loci, or a contiguous set of bases) that are deleted. Thus, one haplotype includes bases in the region and the other haplotype is missing bases in the region. Linking can allow the determination of amounts of sequence reads at the region for both haplotypes. When the amount of reads for one haplotype is very low (e.g., with respect to the amount for the other haplotype), then a deletion can be identified.

Figure 10:
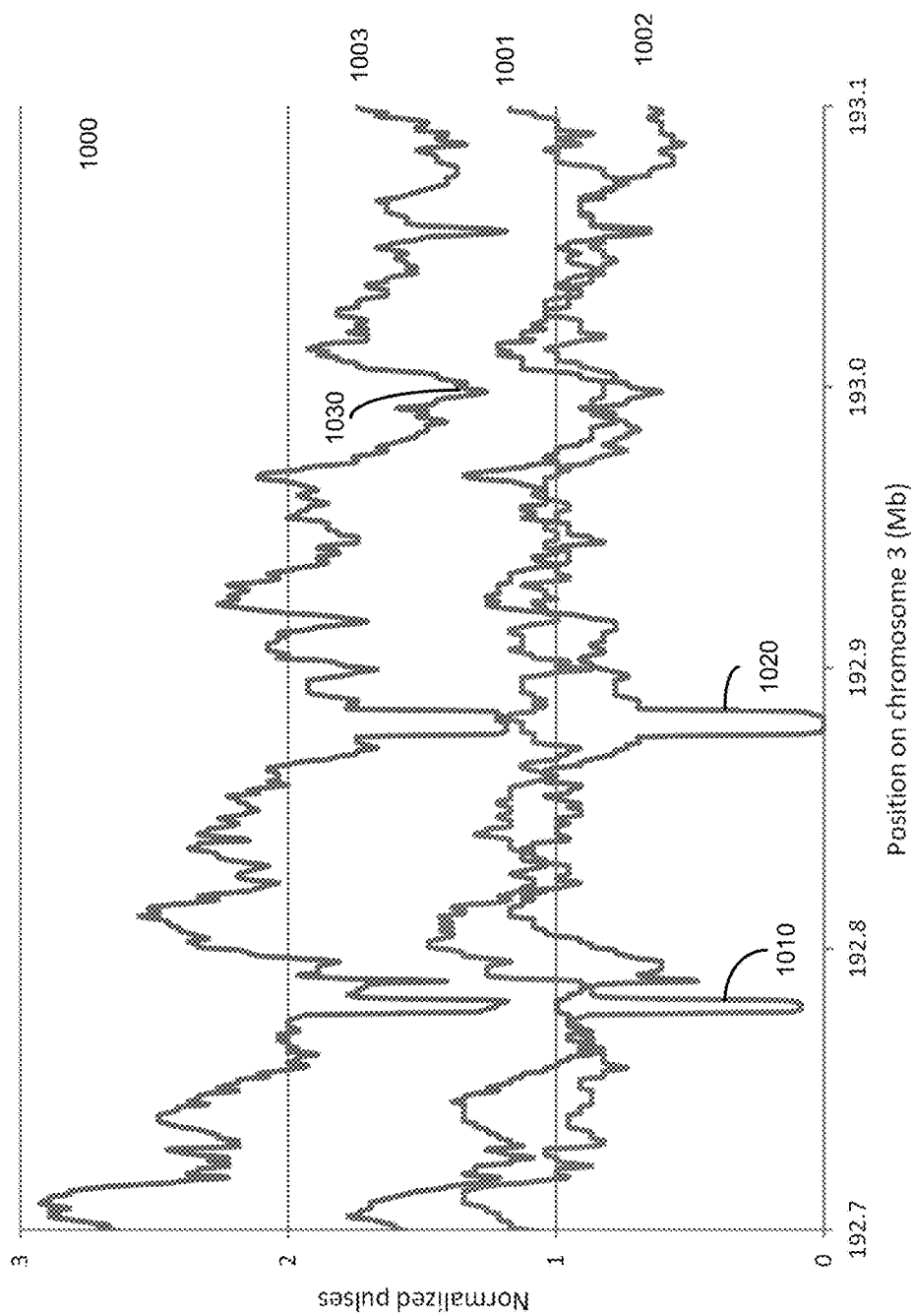
FIG. 10 shows a diagram 1000 of binned coverage per haplotype for hemizygous deletion detection according to embodiments of the present invention.

FIG. 10 shows a histogram 1000 for hemizygous deletion detection according to embodiments of the present invention. The vertical axis corresponds to a count for the amount of reads (also referred to as coverage) at different regions (horizontal axis). Specifically, the amount is a normalized amount of pulses, e.g., where a pulse corresponds to an estimate of a reconstructed long fragment. Histogram 1000 shows the normalized coverage from each haplotype (blue: parent 1001, and red: parent 1002) and coverage from

TABLE 2

|  | Rep. 1 expanded | Rep. 2 expanded | Shared | % rep. 1 shared | % rep. 2 shared | Phasing rate |
|---|---|---|---|---|---|---|
| All homozygous SNPs | 1,301,842 | 1,304,031 | 1,165,691 | 89.5 | 89.4 | — |
| Linked homozygous SNPs | 1,077,756 | 992,089 | 962,745 | 89.3 | 97.0 | 82.6 |

The lower linking rate of 82.6% (compared to the phasing rate of 98% for heterozygous SNVs) is expected due to >20% of genomic regions not covered by LFR contigs (Table 300). This phenomenon has previously been described and is caused by regions of low heterozygosity (RLHs, genomic regions of 30 kb with less than 1.4 heterozygous SNPs per 10 kb) covering ~30% of this genome. Thus, the ability to link a locus in a RLH is reduced relative to other regions.

De novo mutations occur with equal regional frequency across the genome. As a result, RLHs also limit detection of phased de novo mutations to ~82.6% of all called de novo mutations or to about 79% of all existing de novo mutations when the overall genomic call rate is considered (0.826 phasing rate×0.96 variant calling rate for replicate 1 of embryo #8). Unphased de novo-like variants are mostly errors (on average we detect greater than 30,000 errors in these libraries and only about ~30 unphased real de novo mutations are expected) and cannot be distinguished. Longer genomic fragments or availability of parental whole genome sequence data are expected to substantially reduce unphased regions resulting from RLHs and increase the detection rate of de novo mutations verified by phasing. For example, the combined haplotypes (green—1003) from replicate 1 of embryo #8, across a 400 kb region of chromosome 3.

The haplotype information can be used to determine separate coverage for each allele. Two deletions detected in this interval are indicated. Deletion 1010 shows a hemizygous deletion of approximately 7 Kb. The coverage for the parent 1001 haplotype drops nearly to zero but the parent 1002 haplotype coverage stays close to 1. Deletion 1020 shows a hemizygous deletion of approximately 10 Kb. The coverage for the parent 1002 haplotype drops to zero, while the coverage across the same region in parent 1001 stays close to 1. Both of these deletions occurred in the region between the MB21D2 and HRASLS genes.

As an example, the separate haplotype coverages can be determined using labels, as described above. For instance, assume that the odd labels correspond to reads of contigs from parent 1001 and the even labels correspond to reads of contigs from parent 1002. If there are only reads with A at a locus, one can determine whether all of the reads come from the even or odd labels or both. If the reads only (or mostly) have even labels, then that can indicate a deletion in parent 1001 haplotype at the locus. The labels and amount of reads can be obtained after linking the locus to hets of one or more contigs. If the reads only (or mostly) have odd labels, then that can indicate a deletion in parent 1002 haplotype at the locus. If the amount of reads from both labels is about the same or above a threshold, then the locus can be identified as homozygous for A, with no deletion.

Without such haplotype information, identifying a deletion can be difficult as the region could simply be homozygous with low coverage. For example, the region 1030 has about the same coverage as region 1020 where the deletion occurs, but there is no deletion in region 1030.

A. Method

Figure 11:
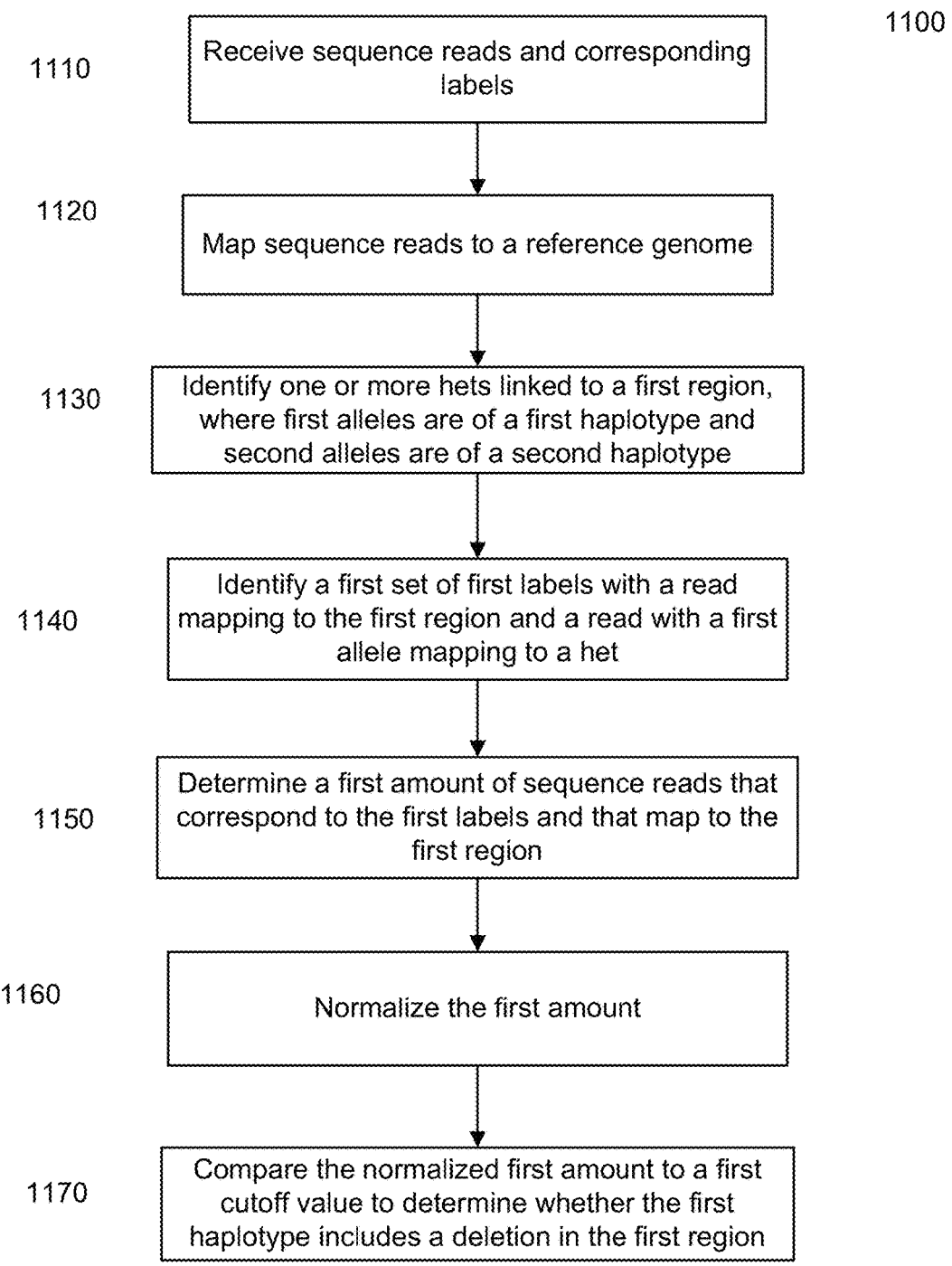
FIG. 11 is a flowchart of a method 1100 of detecting a hemizygous deletion in a genome of an organism by analyzing a sample obtained from the organism according to embodiments of the present invention.

FIG. 11 is a flowchart of a method 1100 of detecting a hemizygous deletion in a genome of an organism by analyzing a sample obtained from the organism according to embodiments of the present invention. Method 1100 can use linking of a region to one or more hets to identify which reads (if any) in the region correspond to which haplotype, thereby allowing a threshold criteria to be focuses on reads corresponding to a particular haplotype. In this manner, a hemizygous deletion can be detected with greater accuracy.

At block 1110, sequence data from a sequencing of a plurality of nucleic acid molecules of the organism is received. The sequence data can be as described herein. For example, the sequence data for each of the plurality of nucleic acid molecule can include one or more sequence reads of at least one portion of the nucleic acid molecule, and a label corresponding to the one or more sequence reads, where the label indicates an origin of the nucleic acid molecule.

At block 1120, at least one sequence read of each of the plurality of nucleic acid molecules is mapped to a reference genome for each of the plurality of the nucleic acid molecules. The mapping can be performed using any suitable techniques, e.g., as described herein.

At block 1130, one or more hets are identified as linked to a first region. Each het has a first allele corresponding to a first haplotype and a second allele corresponding to a second haplotype. The linking of the first region to the one or more hets can be identified according to embodiments described above, e.g., using a number of shared labels and/or a contig being within the region. When more than one het is used, the hets can be phased so that one allele of a first het is known to be on the same haplotype of a second het. These hets can be called phased hets. In various embodiments, the first region can be defined by one or more specific loci (i.e., as corresponding to the one or more specific loci), separate areas around the loci, by the region between a first and last locus, or a region of contiguous positions.

At block 1140, a first set of first labels is identified. These first labels are shared between the first region and the first haplotype. Thus, each first label corresponds to one or more sequence reads mapping to the first region of the reference genome. Each first label also corresponds to at least one sequence read mapping to one of the identified hets and including the corresponding first allele.

In one embodiment, a set of first aliquots having sequence reads mapping to the first region can be identified as the first labels, e.g., barcodes that correspond to the aliquots. Thus, a sequence read mapped to the first region can be associated with at least one other aligned sequence based on a presumption that the two sequence reads are potentially derived from a same fragment of DNA. The presumption can be based on the two reads coming from a same aliquot.

At block 1150, a first amount of sequence reads that correspond to the first labels and that map to the first region is determined. In various embodiments, the first amount can correspond to the number of labels, all of the reads mapping to the first region and having one of the first labels, or a count of the number of reads that map to the first region and to a the minimum number of hets on the first haplotype for each label.

At block 1160, the first amount is normalized to obtain a normalized first amount. The first amount can be normalized in various ways. For example, the first amount can be normalized based on an amount of sequencing performed, a number of cells in the sample, or the amount of sequence reads corresponding to the second haplotype.

In one embodiment, a second set of second labels is identified. These second labels would be shared between the first region and the second haplotype. Thus, each second label corresponds to one or more sequence reads mapping to the first region of the reference genome. Each second label also corresponds to at least one sequence read mapping to one of the identified hets and including the corresponding second allele. As examples, the normalized first amount can be a ratio or a difference of the first and second amounts, which includes a ratio of functions of the two amount (e.g., a ratio of a sum of the two amounts and one of the amounts).

At block 1170, the normalized first amount is compared to a first cutoff value to determine whether the first haplotype includes a deletion in the first region. The first cutoff value can be determined dynamically and also be dependent on an amount of sequencing performed and a number of cells in the sample. The determination can have various classifications as to a likelihood of a deletion, which can correspond to different cutoff values. For example, a higher cutoff value can indicate a higher likelihood of a deletion than a lower cutoff, i.e., when the normalized amount exceeds the respective first amounts. Classifications can include indeterminate, positive, and negative for a hemizygous deletion, along with different gradations of positive or negative.

In one embodiment, the first amount (first haplotype) can be compared to the second amount (second haplotype) to determine a classification of whether a hemizygous deletion exists. In one embodiment, a difference can be taken between the first amount and the second amount, and the difference can be compared to one or more cutoff values. The various cutoff values can correspond to difference classifications. In another embodiment, a ratio can be taken between the first amount and the second amount, and the ratio can be compared to one or more cutoff values.

As the sequence reads of the region can be for hets or homozygous loci, deletions can be found regardless of the genetic structure. Some example cutoff values are 10% of the average coverage for a haplotype for normal regions, or 20% of the amount of the other haplotype.

The first region can be of various sizes, and the limits of the deletion can be explored. For example, after a first locus (e.g., a single position) is determined to have a deletion, then neighboring loci can be investigated to determine if there is a deletion at the neighboring loci. The size of the deletion can be found from the consecutive loci identifying the deletion. To use one or only a few loci, the sequencing depth may need to increase to obtain a desired confidence/accuracy.

In one implementation, one can use a sum of multiple loci to determine the amount for the first region. As an example, the individual loci can be required to satisfy one criteria (e.g., a first threshold) and the sum over the loci need to satisfy another criteria (e.g., a second threshold). One can normalize based on number of loci to determine appropriate cutoff. One can also normalize based on the total reads for the loci, or the total reads including other regions of the genome.

B. Exon Deletions

Some embodiments are directed to identifying deletions in exons. In one implementation, exon areas can be sampled at intervals of 20 bases within certain regions (i.e., within exons), which is a relative dense sampling compared to sampling every 1,000 bases. The exons can be identified from a database, such as NCBI. The intervals could be any value, including every base. The sampling in an exon can be used as the first region from method 1100. It can even have one sample per exon, but higher density can provide more confidence. With this sampling for exon areas, which are about 5% of the genome, there is a denser representation than is generally done for general deletions, as described later.

In one embodiment, each sampling locus can be tested for whether there is a deletion. In another embodiment, a set of loci can be tested together. For example, the amounts of reads from a particular haplotype can be summed across the set of loci.

In an example sampling every 20 bases, an average of one to five sampling loci is obtained for every exon. Averages or median for the length of exon is about 30 to 100 bases. In one embodiment, if there are three loci on the exon that are being analyzed to detect a deletion, a sum of the number of counts from one haplotype can be compared to the sum of the counts for each of those three on the other haplotype.

In another embodiment, each of the three loci can be tested separately. In one implementation, only fragments aligning to the 3 loci are counted. In another implementation, any fragments aligning to any location in a region (e.g., between the loci or in a window around the loci) can be counted. The count can be a number of wells or a number of sequence reads from the wells, or other values mentioned herein.

In some embodiments, it can be assumed that the exon is deleted in total. In other embodiments, part of the exon can be deleted which can be detected by looking at a smaller region than the entire exon. As counts can be retained for each locus, the sum for any subregion can be computed. Thus, if one locus exhibits a deletion and another locus does not exhibit the deletion, then part of the exon can be identified as being deleted. In one aspect, embodiments may not know whether the deleted haplotype is from the mother or the father, just that one is missing.

Figure 12:
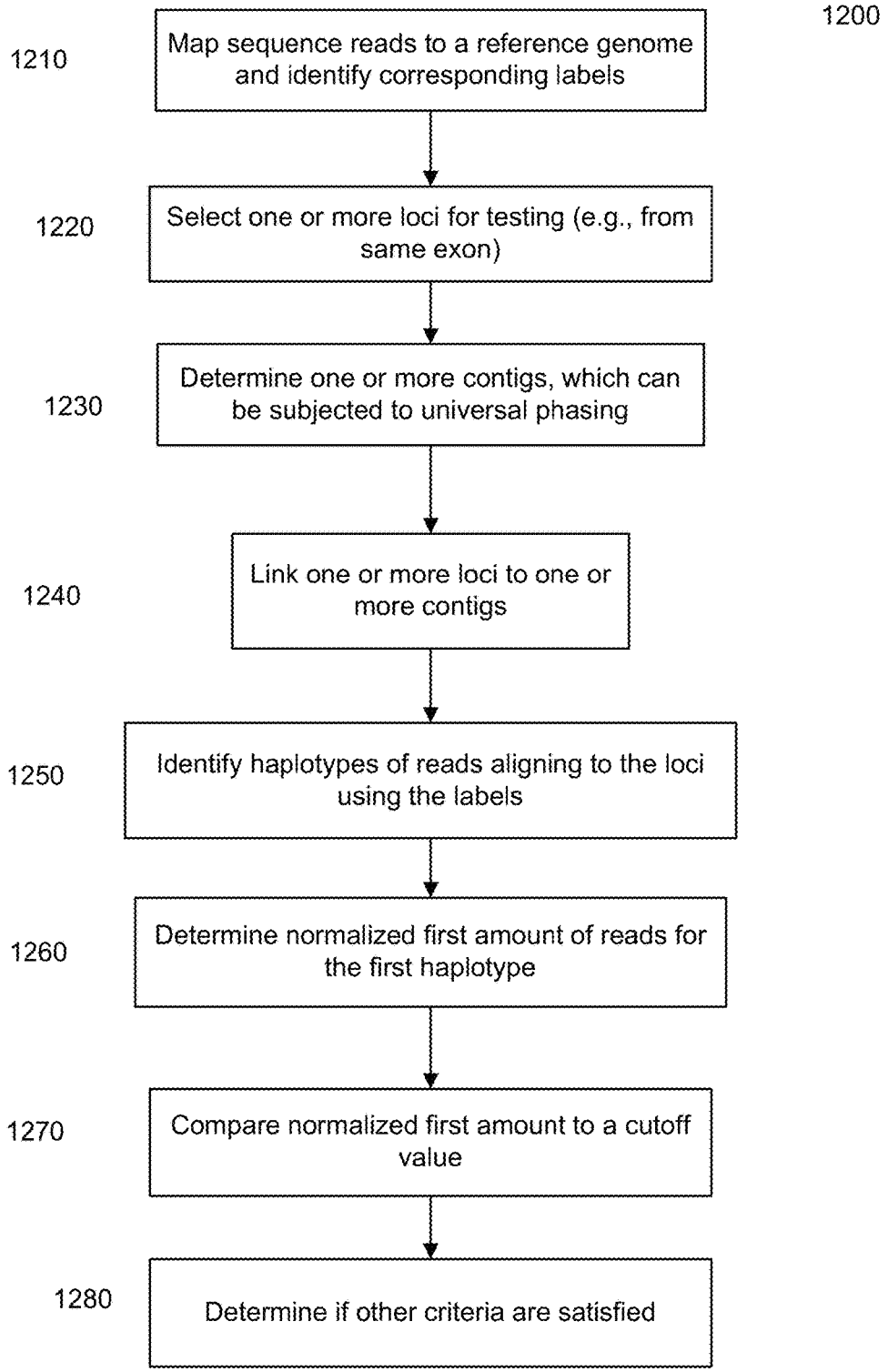
FIG. 12 is a flowchart of a method 1200 for identifying exon deletions according to embodiments of the present invention.

FIG. 12 is a flowchart of a method 1200 for identifying exon deletions according to embodiments of the present invention. Method 1200 can, for example, identify exon deletions of 20 by to 2 Kb. In one embodiment, the original long fragments were processed by first filling the internal fragment gaps of 2 Kb or less, and then by eroding 0.5 Kb from each end. The long fragments can then fragmented to provide the nucleic acid molecules for sequencing.

At block 1210, sequence reads are mapped to a reference genome and corresponding labels are identified. The mapping may be performed by any suitable technique, e.g., as described herein. The labels can be identified as described herein.

At block 1220, one or more loci are selected for determining whether a deletion exists at the loci. In various embodiments, the loci can correspond to any combination of different parts of the same gene, different parts of the same exon, different exons of the same gene, or different genes. These loci can correspond to the first region in method 1100.

At block 1230, one or more contigs are determined. The contigs can be subjected to universal phasing. The contigs can be determined by phasing hets to obtain contigs with alleles identified as being from a first haplotype or a second haplotype. When there are multiple contigs, the first designation of haplotype is only consistent within a contig. That is, the first haplotype of one contig is not necessarily the same (from the same parent) as the first haplotype of another contig. The universal phasing can be used to match haplotypes from different contigs, and thus identify one haplotype as being from the mother and the other haplotype being from the father. The universal phasing can be performed by identifying alignment of contigs for overlapping regions of the contigs.

In one embodiment, the phasing of the hets can use pulses, which correspond to estimates of reconstructed long fragments from a particular aliquot. These pulses can be labeled as being from the first parent (e.g., mom) or the second parent (e.g., dad) based on which haplotype the pulse is consistent. For example, the alleles of a pulse can be compared to that of the two haplotypes to determine the corresponding haplotype. A pulse can be phased by identifying the corresponding haplotype. In this embodiment, one haplotype of a contig can be longer than the other haplotype of the contig.

At block 1240, the one or more loci are linked to one or more contigs (or just one het). The loci can be linked to the contig via techniques described herein. In one embodiment, the linking can be identified based on a pulse covering a locus or being within a specified window around the locus. The linking criteria can identify loci (or other regions) that were not accessible. For example, 20% of the regions may be identified as not being assessable.

At block 1250, the corresponding haplotypes are identified for the reads aligning to the loci using the labels. For example, if a read has a label that corresponds to a first haplotype, then the read can be identified as being from the mother. And, if the read has a label that corresponds to a second haplotype, then the read can be identified as being from the father. A read can also be identified as being from both (if there is a conflict), where such a read can be excluded. If a locus was not linked, then a no parent designation might be made. In one embodiment, the haplotype of a read can be identified by a pulse aligning to one of the linked loci.

At block 1260, a normalized first amount of reads for the first haplotype is determined. The normalized first amount can correspond to a number of labels, and be normalized by the number of corresponding loci (i.e., number of identified loci at block 1240) and by a number of contigs. Other normalized values can be computed, e.g., to ensure a sufficient read coverage of the loci so as to avoid regions of low accuracy and to avoid false positives for a deletion.

In various embodiments, the following values can be computed. The "normalized phased wells" (NPW) can be computed for each haplotype (i.e., one value for hap1 and another value for hap2). The NPW for each haplotype is determined as the ratio of the phased wells for the haplotype and the number of corresponding loci (which compensates for when more loci are used). The number of phased wells for hap1 corresponds to the number of wells having a read at one of the linked loci and having a read that corresponds to a phased het (i.e., a het of a contig) of hap1 of a contig. The number of phased wells for hap2 can be computed in a similar manner. In one implementation, NPW can provide an average number of phased wells per locus.

The "ratio of normalized phased wells" (RNPW) corresponds to the maximum of the two possible ratios of the two NPWs, i.e., the ratio that is greater than 1. For example, if RNPW1 corresponds to hap1 and RNPW2 corresponds to hap2, then RNPW corresponds to the larger of RNPW1/RNPW2 and RNPW2/RNPW1.

The "normalized region phased wells" (NRPW) can also be computed for each haplotype. A region can correspond to uniformly distributed regions (bins) of specified length (e.g., 1 Kb). A region can include all or some of the loci. The NRPW for a haplotype is the number of phased pulses for the haplotype divided by the number of loci in the region. For a haplotype, the number of phased pulses for a bin corresponds to the number of unique pulses that overlap with the bin, correspond to the haplotype, and overlap with a contig (e.g., one or more phased hets of the contig). The "ratio of normalized region phased wells" (RNRPW) corresponds to the maximum of the two possible ratios of the two NRPWs, i.e., the ratio that is greater than 1. As an example, then RNRPW corresponds to the larger of NRPW1/NRPW2 and NRPW2/NRPW1.

The "double-normalized phased wells" (DNPW) can also be computed for each haplotype. For a given haplotype, DNPW is the ratio of NPW to NRPW for the same haplotype. DNPW can provide a ratio of shared wells for the loci relative to shared pulses for a region including at least a portion of the loci. For a region without a deletion, DNPW would be about 1. Also, if the entire region is deleted, then DNPW would be relatively large as both NRPW and DNPW would be small (e.g., both 0, which can be taken as 1). The "ratio of double-normalized phased wells" (RDNPW) corresponds to the maximum of the possible ratios of the two DNPWs, i.e., the ratio that is greater than 1).

In various embodiments, the ratio of normalized phased wells, the ratio of normalized region phased wells, or ratio of double-normalized phased wells can be used as the normalized first amount. Using a ratio can compensate for when more cells are used, and thus more phased wells or phased pulses result. Using RDNPW allows larger deletions to be excluded (i.e., when a contiguous region is deleted, as opposed to just the loci). Also, RDNPW allows deletions of both haplotypes to be avoided since the ratio will be about 1, since the DNPWs for both haplotypes will be similarly low. These other types of deletions can be detected in other ways. And, this implementation can allow for the detection of how localized the deletion is.

At block 1270, the normalized first amount is compared to a cutoff value. In one embodiment, the double-normalized phased wells is compared to a cutoff value (e.g., between 5-15, such as 10). Other normalized amounts can be used, as described herein.

At block 1280, the loci can also be analyzed further to determine if they satisfy further criteria. Block 1280 can be performed before or after block 1270. When performed before 1270, the further criteria can specify whether a locus is assessable. In one implementation, only those assessable loci are then be analyzed in block 1270. Block 1280 can be optionally done to avoid areas of low coverage, effectively no call regions for deletions. In one aspect, assessable loci correspond to regions where a determination of a deletion can be made. A false positive might arise if non-assessable loci are analyzed further.

As examples, the maximum of the normalized phased wells can be required to be greater than a threshold. Also, the normalized region phased wells can be required to be less than a specific value, such that the coverage of one haplotype is not significantly different, except for the possible deleted region. Various logical combinations of criteria can be used. In one embodiment, the logical combination of criteria is (a AND b) AND ((c AND d AND e) OR f), where:

a) The locus belongs to a phased contig (i.e., locus is part of the contig or is linked to a phased contig).

b) Number of loci is greater than or equal to a specified number (e.g., 1).

c) The maximum of the normalized phased wells is greater than or equal to 6 (e.g., to ensure sufficient coverage for the haplotype that does not include a deletion).

d) The minimum of the normalized region phased wells is greater than or equal to a specified number. A larger value can filter out large deletions of an entire region so only smaller exon deletions are detected. A value of zero would not act as a filter.

e) The ratio of normalized region phased wells is less than or equal to 3. (e.g., to make sure the region is relatively balanced).

f) Maximum of normalized phased pulses is less than 6 AND minimum of the normalized phased pulses is greater than or equal to 2. Other values may be used and may change based on the size of the sample (e.g., number of cells). This can make sure the number of phased pulses fall into a balanced set of bounds, and therefore avoid areas that could potentially fool the deletion detection logic.

Some results are provided for the analysis of embryos. The attempted fractions (percent assessable) for embryo #8 replicates 1 and 2, embryo #13, and control libraries were 80.7%, 70.6%, 61.8%, and 58.5% respectively. Embodiments identified 4 exon deletions in 4 genes in embryo #8 library 1; 6 exon deletions in 6 genes in embryo #8 library 2; 7 exon deletions in 7 genes in the library generated form embryo #13; and 6 exon deletions in 6 genes in the blood cell control library.

Only two exon deletions were detected in both the replicate libraries generated from embryo #8. We examined the 2 deletions detected in the replicate 1 that were not identified in the replicate 2 library, and found that one was declared as assessable (i.e., greater than a cutoff) in the second library for replicate 1. However, the average "ratio of double normalized phased pulses" for this deletion was 7.2, i.e., high but below the threshold of 10 used for the additional criteria.

In one embodiment, a higher density sampling can be performed in exons, but a coarser sampling (e.g., every 10,000 bases) can be performed for any part of the genome. For example, starting from the beginning of every chromosome to the end of it, embodiments can sample every 10,000 bases (or other rate).

C. Long Deletions

Some embodiments are directed to identifying long deletions. In these embodiments, the genome can be broken up into bins of a specified length, e.g., 0.5 Kb. Thus, embodiments can sample all the 500 bases in the same region, with the 500 bases of a region being considered as a single point by counting any pulse within the window with equal weight. For example, for a particular 500-base region (i.e., 500 contiguous bases), for every base of the pulse that corresponds to the mother haplotype, a counter can be incremented by one. In other embodiments, the amount of overlap of the pulse within the region can be used to provide different weights. In one implementation, one can divide the sum by 500 (or whatever the length of the window may be) to get an average representation for the counts of pulses and a bin.

Figure 13:
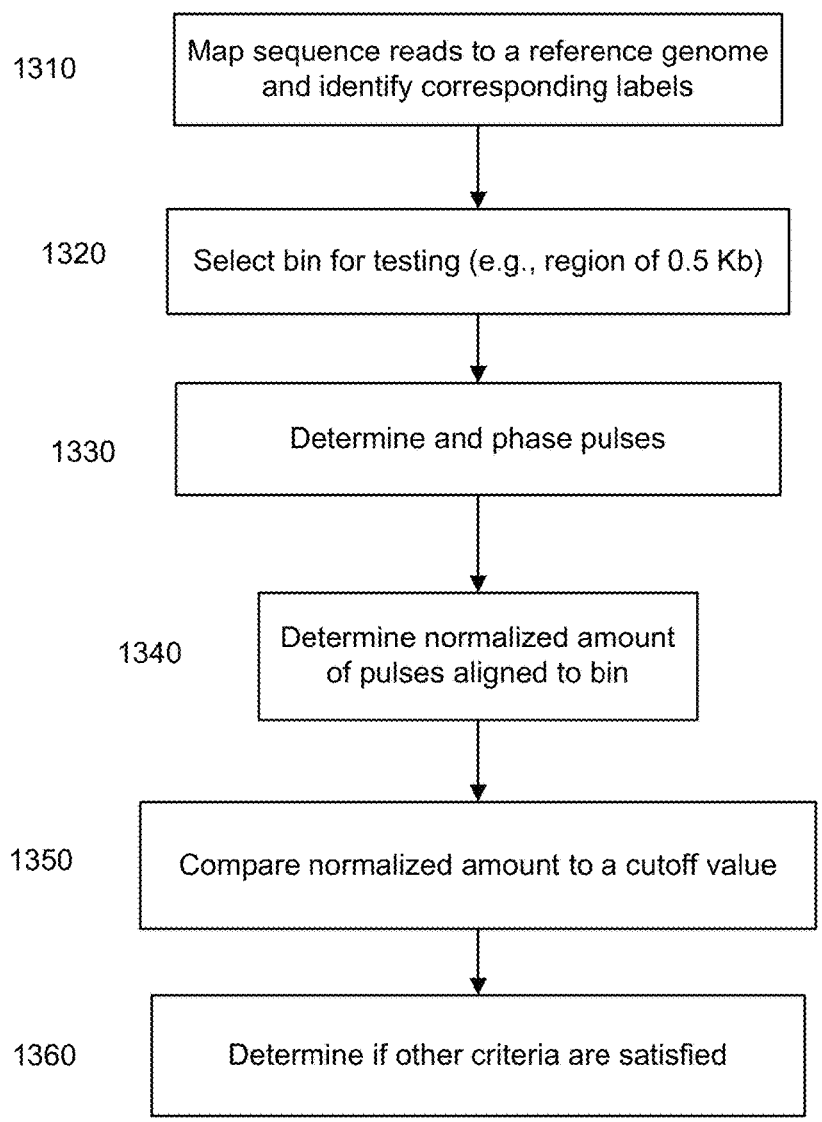
FIG. 13 is a flowchart of a method 1300 for identifying long deletions according to embodiments of the present invention.

FIG. 13 is a flowchart of a method 1300 for identifying long deletions according to embodiments of the present invention. Method 1300 can, for example, identify long deletions of 1 Kb to 40 Kb.

At block 1310, sequence reads are mapped to a reference genome and corresponding labels identified. The labels can be used to identify reads that are from a same well. Reads that are from a same well and that are close to each other can be used to create a pulse. In one aspect, although multiple reads having a same label can align to the same genomic position, such reads can be treated as contributing to a single pulse. Such reads can result from amplification of fragments, thereby having multiple reads at a same genomic position. Thus, embodiments can have a label contribute only a coverage of one to any part of the genome.

At block 1320, a bin (region) is selected for determining whether a deletion exists in the bin. The bin can correspond to any contiguous region of consecutive genomic positions, e.g., 0.1 Kb to 1 Mb, such as 0.5 Kb, can be used as the bin size. The bins can be non-overlapping, and be consecutive, such that a new bin is encountered at specified intervals (i.e., every N bases, where N is the bin size).

At block 1330, a plurality of pulses are determined and phased. A pulse is created from reads having a same label, and thus a pulse is associated with a particular label. More than one pulse can be associated with the same label, e.g., pulses that correspond to different parts of the genome, each pulse for a different long fragment in the well.

Once the pluses are determined, the pulses with various labels can be phased. The phasing can identify which haplotype a pulse is from, e.g., whether the pulse is from the mom or dad. The phasing can be done in a variety of ways. For example, an overlapping of two pulses (e.g., common alleles at multiple hets) can be used to identify pulses that are from a same haplotype.

At block 1340, a normalized amount of pulses aligning to the bin is determined. A pulse can be considered to be aligned to a bin if the pulse aligns to any position within the bin. For example, if the last base of a pulse aligns to the first position of a bin, then the pulse can be identified as aligning to the bin. Other embodiments can require a higher number of overlapping bases before alignment is identified. In one embodiment, the normalized amount of pulses can be a phasing rate that is determined as the number of phased pulses divided by the total number of pulses that are at least partially within the bin.

Other examples of the normalized amounts of pulses and examples of other values, which may be determined for each bin, include the following. The normalized total pulses (NTP) can be calculated as the total number of pulses divided by a normalization factor (e.g., the mean of the total pulses for the candidate bins). Candidate bins correspond to the bins being analyzed or a further subset satisfying specified criteria. The normalized phased pulses (NPP) for a haplotype correspond to the number of the phased pulses divided by the normalization factor used in normalizing the total number of pulses. Normalized adjusted pulses (NAP) corresponds to the number of normalized total pulses minus the minimum of the two normalized phased pulses (i.e., for each haplotype), where the minimum would correspond to haplotype that has a deletion (if one exists).

A counter can determine the number of pulses aligning to a bin. For example, a counter can be incremented each time a pulse is found to align to a bin. A counter can be used for each haplotype. Counters can be used for determining any amounts described herein.

In one embodiment, a number of contigs within the bin can be determined. For example, a bin can have one contig at one end, and another contig at the other end. Depending on the size of a bin, a bin could have more than two contigs (e.g., one in the middle), but it would be unlikely. In one implementation, bins with more than 1 contig can be discarded from analysis. In other implementations, the number of contigs can be used to normalize the amount. For example, a bin having two contigs could be normalized by a factor of two, since the number of pulses would be expected to be greater due to the two contigs being within the bin.

A polyN is a sequence of no calls (N), which can act as a placeholder for a missing sequence. The value of N can be required to be larger than a threshold to be considered a polyN. A polyN can be a binary value for each bin, where the polyN value indicates the presence of at least one reference genome polyN base in the bin. The polyN value can be used to invalidate the bin from the list.

At block 1350, the normalized amount is compared to a cutoff value. The normalized amount can correspond to the haplotype with fewer pulses. The comparison can determine whether the bin is a candidate for including a deletion, with additional criteria being used to make the final determination. The comparison can also determine that the bin does have deletion, without the need for additional criteria.

In one embodiment, the minimum of the two NPPs is compared to a first cutoff (e.g., 0.15). In combination with this criterion or as a different criterion, the absolute difference of the two NPPs can be constrained to be greater than or equal to 0.7. Thus, the cutoff value can be dynamically determined and can depend on an amount of pulses for the other haplotype. In yet another embodiment, the NAP can be required to be greater than or equal to 0.9. Any of these conditions (and/or other conditions) can indicate that the number of pulses for the two haplotypes is significantly different, which can indicate a deletion.

At block 1360, it is determined whether the bin satisfies other criteria, e.g., which may qualify a bin as a candidate bin. Some or all of the other criteria can be applied to a bin before or after block 1350. In one embodiment, candidate bins are selected based on the following criteria: (a) Not a Polyn bin AND (b) Total number of pulses for current bin is greater than or equal to half of the mean of the total pulses for all bins AND (c) Phasing rate greater than or equal to 70% for current bin. In one implementation, these criteria can be used to identify candidate bins, and then other criteria can compare the normalized amount to a cutoff, as well as other conditions. Blocks can be performed in various orders. For example, block 1360 can be performed before block 1350.

In another embodiment, the following set of criteria can be used for the conditions in blocks 1350 and 1360 (and may be combined with other conditions). Among the candidate bins, those with the following characteristics can be identified as deletions: (a) Normalized total number of pulses greater than or equal to 0.5 (which can discard bins with relatively low coverage, e.g., as those bins cannot be accurately assessed); AND (b) Minimum of the two normalized phased pulses less than 0.15 (which can the cutoff to determine a deletion exists, subject to other criteria for filtering out false positives); AND (c) Maximum of the two normalized phased pulses between 0.5 and 1.5 (which can discard bins with relatively low coverage or too high coverage); AND (d) Phasing rate greater than or equal to 0.5 (which can ensure that the bin is linked to a contig with sufficient accuracy); AND (e) Absolute difference of the two normalized phases pulses greater than or equal to 0.7 (which can also filter out regions of low coverage, e.g., if minimum is 0.15 and maximum is 0.5, by ensuring that one haplotype is represented significantly more than the other haplotype in the region); AND (f) NAP greater than or equal to 0.9 (which can also provide similar functionality as (e)). Such criteria can be chosen such that a bin with both haplotypes deleted would not pass the criteria.

Some results are provided for the analysis of embryos. Candidate regions spanning 48.8%, 52.3%, 47.4% and 22.6% of the genome from libraries generated from embryo #8 replicate 1, embryo #8 replicate 2, embryo #13, and the control blood cells, respectively, were identified. From these candidate regions, an embodiment identified 106 deletions in the library generated from embryo #8 replicate 1, 452 deletions in embryo #8 replicate 2 library, and 926 deletions in the embryo #13 library. The algorithm also identified 169 deletions in the control library made from 5 blood cells. The algorithm's thresholds were tuned for a 10-cell library; therefore we expect the numbers for embryo #8, replicate 1 to be more accurate.

D. Extra Long Deletions

If the length of the deletion is more than 2× the fragment length, there would be no phased fragments to show the phenotype that was demonstrated before (one copy normal, one copy dropped to zero). Instead, due to a lack of phasing (across the large gap), both phased copies would approach zero. Nevertheless, embodiments can use a signature that could be used to identify an extra-long one-copy deletion. This can be shown by an example.

Figure 14A:
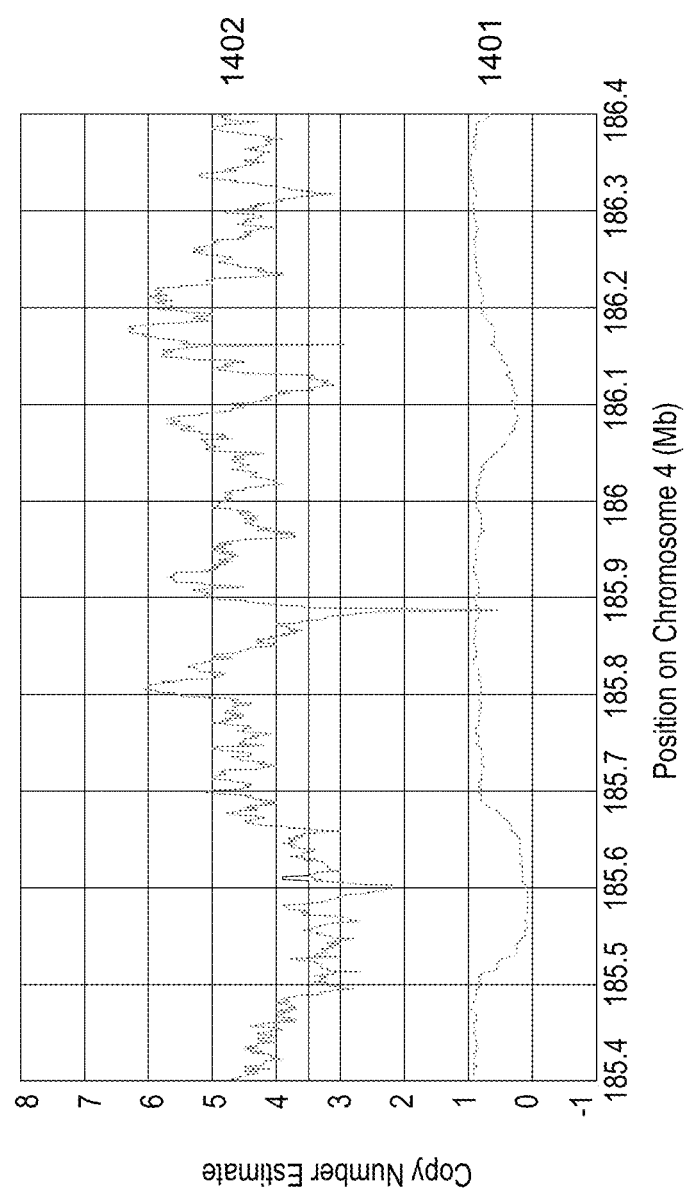
FIG. 14A depicts a phasing rate and a total number of pulses indicating a long deletion (~200 Kb) between 185.5 and 185.7 according to embodiments of the present invention.

FIG. 14A depicts a phasing rate and a total number of pulses indicating a long deletion (~200 Kb) between 185.5 and 185.7 according to embodiments of the present invention. This deletion can be identified as follows (using values describe above for method 1300):

1. Phasing rate 1401 (blue line) dropping to almost zero, AND
2. Total number of pulses 1402 (green line) decreasing across an interval.

The phasing rate could drop to almost zero due to the loss of either one or both chromosomal copies. As phasing identifies both haplotypes, losing one haplotype can cause a lack of phasing for an extra long region. However, since the total number of copies does not drop to zero, it means that one copy is present. Therefore, this is a hemizygous deletion. The loss of phasing can result from a lack of observable hets in the region, since only one allele would be seen for a hemizygous deletion.

Figure 14B:
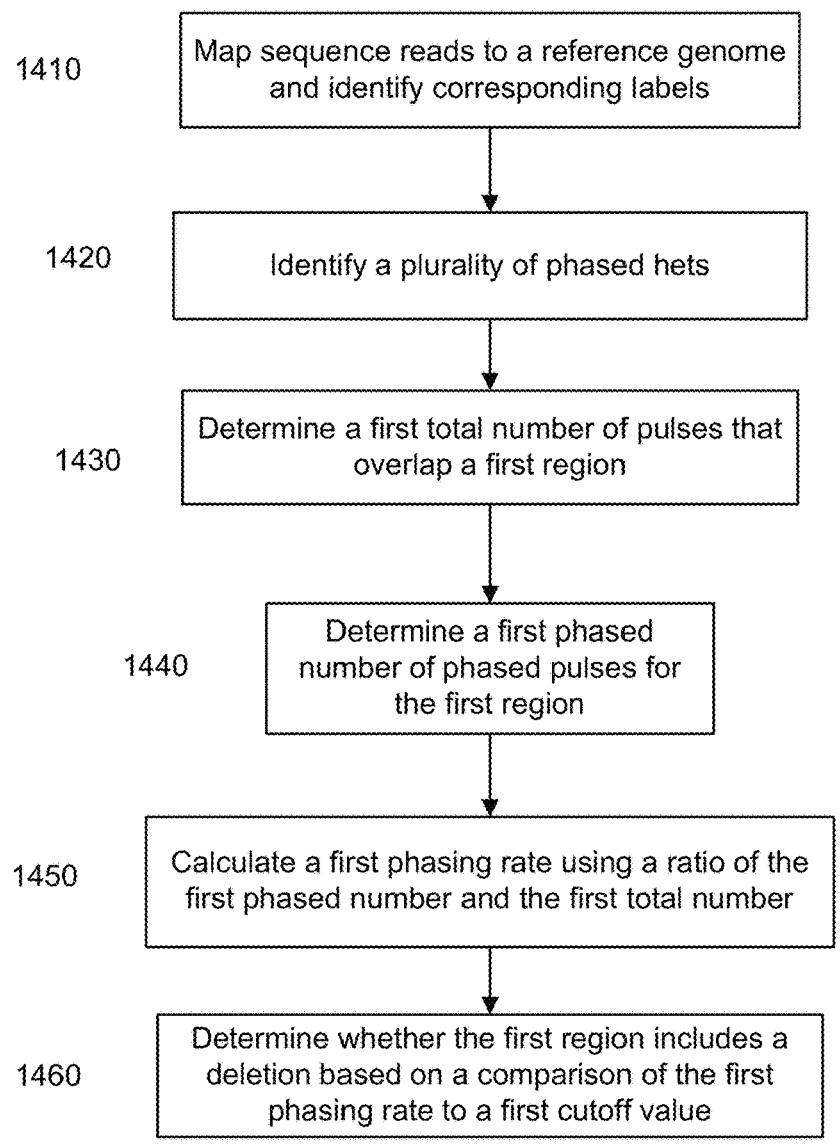
FIG. 14B is a flowchart of a method 1400 for identifying an extra long deletion according to embodiments of the present invention.

FIG. 14B is a flowchart of a method 1400 for identifying an extra long deletion according to embodiments of the present invention. Parts of method 1400 may be implemented as described for other methods herein.

At block 1410, sequence reads are mapped to a reference genome and corresponding labels identified. Block 1410 may be implemented as described for other methods herein.

At block 1420, a plurality of phased hets are identified. Each phased het has a respective first allele for a first haplotype and a respective second allele for a second haplotype. Identifying the plurality of phased hets can include phasing a plurality of hets, or just reading the phased hets from a file. The phased hets can be identified using any suitable technique, e.g., as described herein.

At block 1430, a first total number of pulses that overlap a first region is determined. A pulse corresponds to a contiguous section of the reference genome covered by sequence reads having a same label. The overlap can be defined to be a specified number of based, e.g., 10 bases or just one base. The deletions detected can be as large or larger than the pulses.

At block 1440, a first phased number of phased pulses is determined for the first region. These phased pulses overlap the first region and cover at least a specified number of phased hets (i.e., the pulse includes the position(s) of the phased het(s)). Examples of the specified number of phased hets that need to be overlapped are any value between 1-10 bases or potentially larger. The phased pulses can be for either haplotype.

At block 1450, a first phasing rate is calculated using a ratio of the first phased number and the first total number. For example, the first phasing rate can be the first phased number divided by the first total number, or the first phased number divided by a sum of the first phased number and the first total number. Other ratios and scaling factors (e.g., weights) can be used.

At block 1460, it is determined whether the first region includes a deletion based on a comparison of the first phasing rate to a first cutoff value. Further criteria can be used, e.g., that the total number of pulses (or total coverage histogram) drops in the region. If the total number of pulses drops to zero, then a deletion of both haplotypes can be determined. If the total number of pulses drops but not to zero, then a deletion of one haplotype (hemizygous deletion) can be determined.

In addition to using the first phasing rate of the first region to determine whether the first region includes a deletion, a second phasing rate of a second region (consecutive to the first region) can be used to determine whether the first region includes a deletion. For example, the phasing rates of both regions can be required to be less than respective cutoffs (which may be the same) for a deletion to be determined. A threshold number of consecutive regions can be required to have a phasing rate below a cutoff value for a deletion to be determined.

E. Insertion/Amplifications

Embodiments can also identify amplifications. For example, the amounts (e.g., of reads or pulses) of each haplotype for a region can be normalized such that a single copy of a haplotype would show up as one, and regions that are amplified would show up as two or more. As another example, if the coverage for both haplotypes is too large to be considered a deletion, an amplification can be identified when a disparity between the first amount for a first haplotype relative to the second amount for a second haplotype is relatively large (e.g., greater than 2, or potentially a slightly lower number, like 1.8). Such an analysis can be performed to identify the parts of the known genome are amplified.

For de novo insertions, embodiments can identify a small dip for the one haplotype near the insertion, as less reads would be able to map to the edges of the junctions for the insertion. In one implementation, a high resolution of sampling points is used (e.g., high number of loci or small bins), or the select loci would need to be near the insertion. For an inversion, this would act as a deletion and an insertion. The deletion can be detected as described above.

In one embodiment, a difference between an insertion and a deletion can be identified. The difference can be identified through a depth in the loss of the coverage histogram (total or haplotype with deletion) and a slope of the loss. For example, a difference between an insertion of a length and deletion of about the same length can be that the decline toward that deleted, or apparent deleted area, would have a different slope for the two cases (with the insertion generally having a smaller slope). For example, the slopes may be similar for insertions and very short deletions, but since the dip is smaller for insertion (as compared to longer deletions), the sum of the slopes from both sides (i.e., both sides of the insertion which effectively appear at same place in reference), should increase the apparent slope for the insertion dip.

In one aspect, an insertion (regardless of the size of the insertion) can result in a shallow depth for the loss when binning is done, since a bin would have some mapped reads around the insertion (whereas a deletion would have reads missing from the one haplotype). The change in slope can result from a mapping module (i.e., that maps to a reference) not tolerating that much of error, so a read in the insertion or the deletion is not mapped. Regarding the lack of mapping, there is more gradual decline for a deletion, as there are some partial losses of arms; and for insertion, the decline would be more abrupt.

For a hemizygous indel, the normal haplotype has good coverage. And, the haplotype with the deletion might have decent clone coverage (not base coverage), if the deletion is small enough that the mate pairs can span the indel. In embodiments where a read or pulse is counted for a bin, the coverage would not dip very low for a deletion. Thus, the dip would be shallow for a small deletion.

However, for a long indel, a mate pair cannot span the long indel. Thus, the coverage will be lower, since the read will not be mapped to the reference genome. Thus, the dip would be deeper. Thus, different cutoff values could be used, depending on the size of indels one is looking for. And, different cutoffs could be used to indicate a likelihood of an indel and a corresponding size.

One embodiment can identify amplifications (e.g., long duplications) using the following criteria. Pulses can be phased, and amounts of pulses in a bin can be determined, as mentioned above. Candidate bins with the following characteristics can be selected and marked as a duplication if all of the these conditions were true: (a) Normalized total number of pulses greater than or equal to 2.5 (this identifies bins with high coverage) AND (b) Minimum of the two normalized phases pulses between 0.5 and 1.5 (This ensures that the minimum is not too low or too high, thereby corresponding to a normalized value around one) AND (c) Maximum of the two normalized phased pulses greater than or equal to 2.0 (at least a duplication); Phasing rate greater than or equal to 0.5 (which can ensure that the bin is linked to a contig with sufficient accuracy) AND (e) Absolute difference of the two normalized phased pulses greater than or equal to 0.9 (sufficient difference to indicate the two haplotypes have different coverage).

F. Normalization/Cutoff

Various types of normalization is described above. For example, the normalization for bin can depend upon a mean value for other bins. Such normalization would depend upon which bins the mean is calculated for. The selection of bins can introduce a bias.

Embodiments can identify regions to exclude, and then the normalization would be calculated relative to the remainder of the genome. For example, if 20% of the bins are excluded, then those 20% would not be used in the denominator for normalization. Thus, the other 80% of the bins can be used as the denominator for normalization. As an example, a region might be excluded because the region has high GC content or because the region has very high or very low counts, which might actually remove some of the regions that actually have deletions.

In one embodiment, a fixed cutoff can be used when the normalization of the amounts is dynamic. A variable cutoff can be used, which is equivalent to a normalization. Accordingly, the normalization can affect what the cutoffs are or equivalently how a difference or ratio is scaled. For example, if no normalization is used, doubling coverage can cause a double in the cutoff.

As to determining a cutoff for a given normalization, embodiments can determine experimentally the variance for normal behavior. For example, the number of standard deviations for typical variance. The cutoff value can be selected based on this experimentally determined variance.

V. DISCUSSION AND EXAMPLES

Here we describe the analysis of the entire embryonic genome by advanced, highly accurate whole genome sequencing (WGS) technologies. Biopsies of up to 10 cells from 7 blastocyst-stage embryos from a couple with a known CTG expansion in the DMPK1 gene causing Myotonic Dystrophy were analysed in 9 WGS tests. 87%-97% of the genome was analysed in each embryo; in a subset of embryos high quality haplotype data were generated using Long Fragment Read (LFR) techniques described above. In these LFR-analysed embryos, we demonstrate a higher level of accuracy with similar sensitivity compared to standard sequencing, sufficient to enable a detailed PGD and potential avoidance of embryos with inherited or de novo disease-causing genetic defects, from point mutations to large structural variants.

We have previously demonstrated the importance of haplotype information in identifying inactivated genes and removing false positive SNVs [Peters, B. A. et al. 2012]. Here we have expanded the use of phasing to show how this type of data can be used for verification of homozygotes, identification of expanded trinucleotide repeats, and measurement of CNV gains and losses. Here, demonstrated ability to detect hemizygotic short exon deletions represents a new WGS achievement enabled by LFR. These analyses, combined with recent ENCODE annotations of regulatory sequences and a rich list of population variants obtained by high quality WGS on a large number of unrelated individuals using the same sequencing chemistry, create a very powerful genome-wide prediction tool. These types of analyses can be expanded from IVF embryo testing to any tissue in which 5 or more cells are available, opening the door to non-invasive prenatal genetic testing and cancer screening from circulating tumor cells or micro-biopsies.

In the examples below, we demonstrate that high-coverage WGS (~100×), made affordable by efficient massively parallel sequencing, combined with LFR for phasing and enhanced accuracy, can be used to identify detrimental SNVs, short insertions or deletions, repeat expansions, mitochondrial mutations, and other larger structural changes in a PDG feasibility test. Without using parental WGS to impute missing variants or remove errors (which would result in unwanted removal of all de novo mutations), we demonstrate 94% sensitivity in phased SNP detection with few phased errors per genome. This enables phasing and thus accurate calling of ~79% of de novo SNPs. Most of the unphased de novo mutations (which are indistinguishable by our current methods from amplification-caused errors) are likely introduced in regions of low heterozygosity occupying ~30% of these genomes in agreement with our previous study [Peters, B. A. et al. 2012] and require longer DNA fragments and further optimization of phasing algorithms. Further, we show that the number of false positive SNVs accumulated as a result of amplifying DNA from a small number of cells dramatically reduces the sensitivity and accuracy of WGS approaches without some form of error reduction such as LFR or limiting WGS to calling only parental variants (BGI companion paper). LFR allows these low error rates and detection of de novo point mutations despite starting with only 4 to 10 cells and performing 20,000-fold MDA amplification, which introduces over 30,000 DNA mutations per sample.

This is the first demonstration that the large majority of de novo mutations, which cause a disproportionally high percentage of genetic defects, can be detected in PGD. The higher cost of LFR libraries (compared to standard libraries) and of sequencing to 100× coverage in this advanced WGS can be offset by not sequencing parental genomes. However, there are further benefits of having parental WGS in addition to phased embryonic genomes, such as the ability to impute the few percent of inherited variants that are not phased by LFR, and improved phasing in RLHs that helps in phasing and verifying more de novo mutations. Because the cost of WGS is expected to further decrease with technology improvements and broad use, and because using parental WGS as the ultimate genetic test also allows implementation of genomic medicine for parents, we believe that future reproductive medicine will include advanced phased WGS of couples (or parents-to-be serving as a carrier screen) and IVF or prenatal embryos. Performing the LFR process in thousands instead of hundreds of aliquots using picoliter reactors may help resolve some special repeats and allow measurement of telomere length for each individual chromosome.

A. Standard WGS from Embryonic Biopsies

To demonstrate the potential of WGS as a method of PGD, 9 sequencing libraries were made from ~10 cell biopsies from 7 different 5 day old blastocyst stage embryos. As a control, another library was made from 5 blood cells from an unrelated anonymous donor. Each library was amplified ~20,000-fold using a modified multiple displacement amplification (MDA) protocol and analyzed on Complete Genomics' DNA nanoarray sequencing platform with single pixel per DNB imaging [Drmanac, R. et al. Human genome sequencing using unchained base reads on self-assembling DNA nanoarrays. Science 327, 78-81 (2010)]. In spite of extensive amplification, coverage was very good for all 10 libraries with 87-97% of the genome having both alleles called (Table 300).

Figure 15:
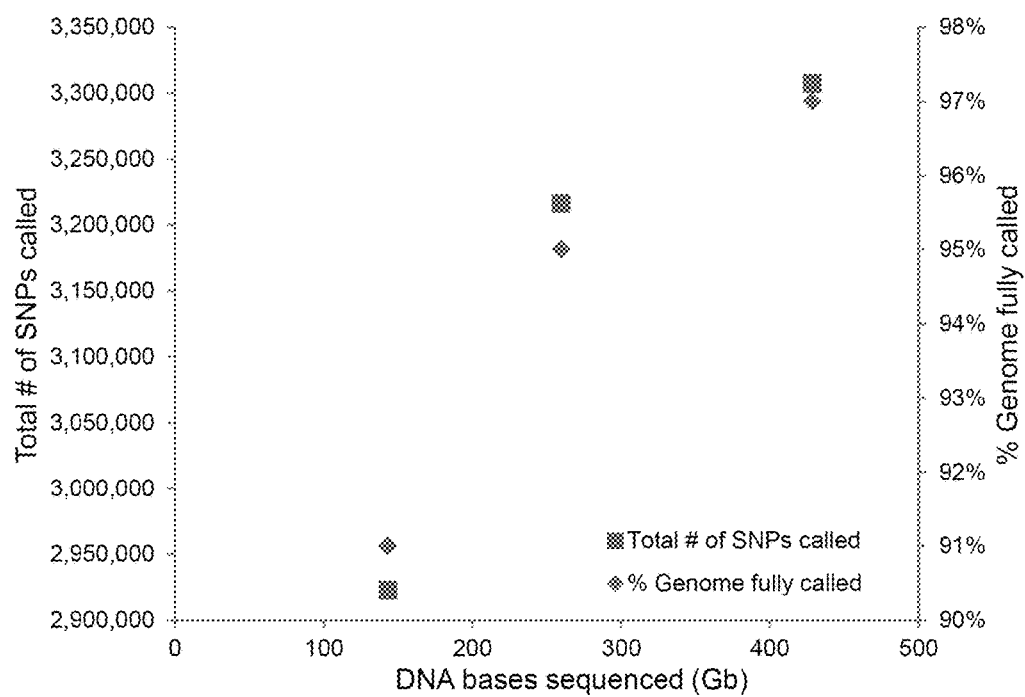
FIG. 15 shows a plot of call rates increasing with increasing bases sequenced according to embodiments of the present invention.

One embryo library (#10) was assembled with different amounts of read coverage; not surprisingly, when more reads were analyzed more of the genome was covered sufficiently to make base calls (FIG. 15). In FIG. 15, not unexpectedly, the more bases sequenced, the larger the total number of SNVs and the higher the total percent of the genome called becomes. The library for embryo 10 was assembled with varying amounts of reads: Complete Genomics' standard coverage of ~50× (143 Gb), their high coverage of ~80× (260 Gb), and a very high coverage of ~140× (429 Gb).

A perfect variation caller would result in the same number of variations after having sufficient coverage. Asymptotic behavior can occur in variation callers, where a few variations are identified at high coverage. This pattern was also observed across libraries made from different embryos (Table 300). Importantly, even in the sample with the least number of total bases sequenced (143.4 Gb), 98% of the genome was covered with 5 or more reads.

The large amount of amplification required to make these libraries affected the quality in two important ways.

Figure 16:
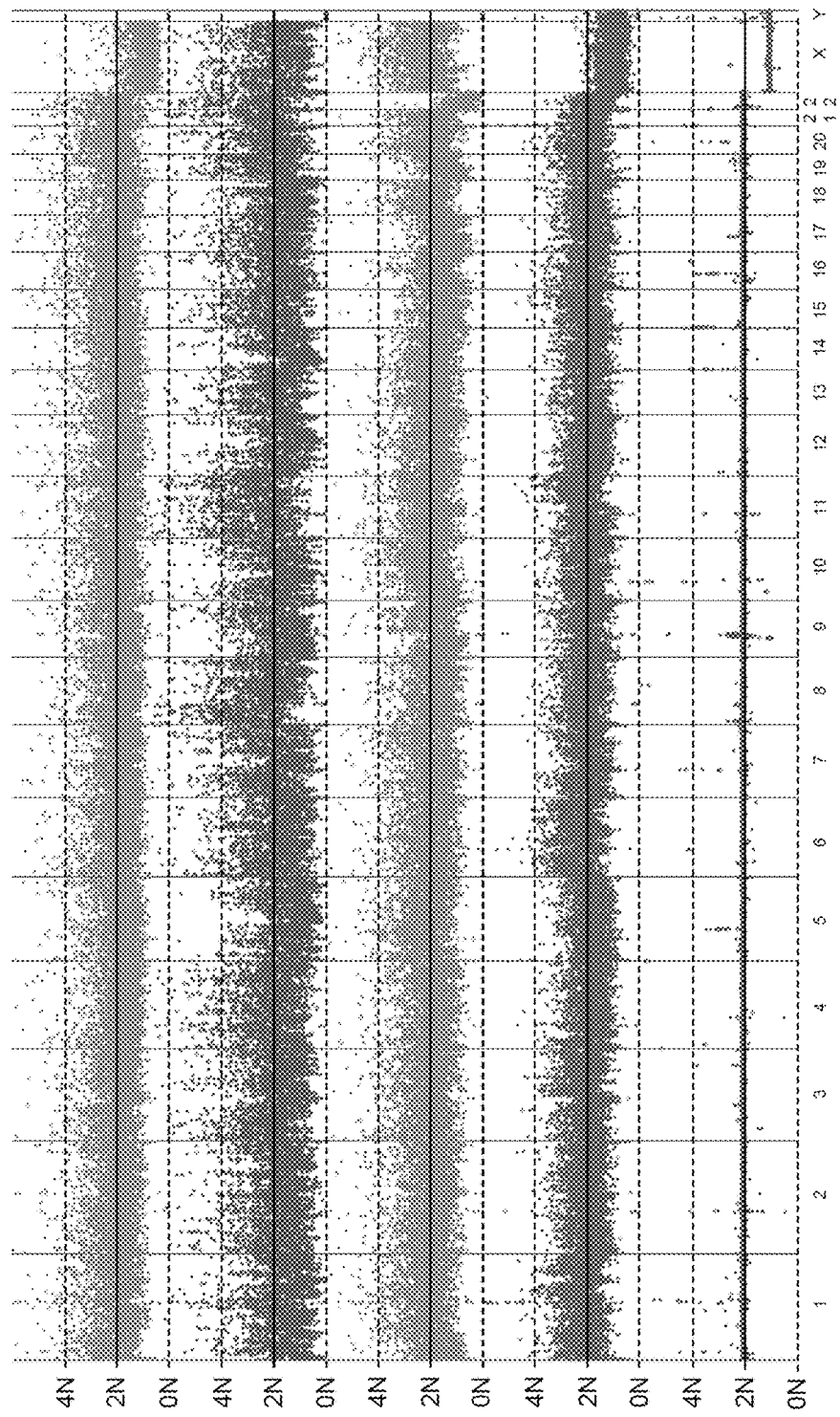
FIG. 16 shows histograms of coverage variability over 100 kb according to embodiments of the present invention.

First, the overall coverage variability across the genome was about 10-fold higher than a publicly released data set (world wide web at completegenomics.com/public-data/) generated on the same platform from a large amount (>5 ug) of high quality genomic DNA (FIG. 16).

Despite this increased noise, large amplifications and deletions could still be detected and used as an embryo elimination criterion. For example, loss of one homologue of chromosome 22 in embryo #13 and chromosome X in the blood cell control are both readily identifiable (FIG. 16). In FIG. 16, coverage was averaged in consecutive 100 kb windows for libraries of embryos #2 (red) and #10 (blue) and LFR libraries of embryo #13 (green) and 5 blood cell control (orange). For comparison sample NA12877 (purple), sequenced as part of a public data release and using our standard process starting from 5 ugs of DNA, was also plotted. Samples were normalized to diploid coverage and offset by 3 units for clarity. Embryo #10 and NA12877 are male as seen by a 0.5× coverage for the X and Y chromosomes. Interestingly, the 5 blood cell control appears to be missing one copy of chromosome X, possibly as a result of Turner Syndrome and embryo #13 is missing a copy of chromosome 22. Both these losses were confirmed by loss of heterozygousity of SNPs.

Figures 17A, 17B:
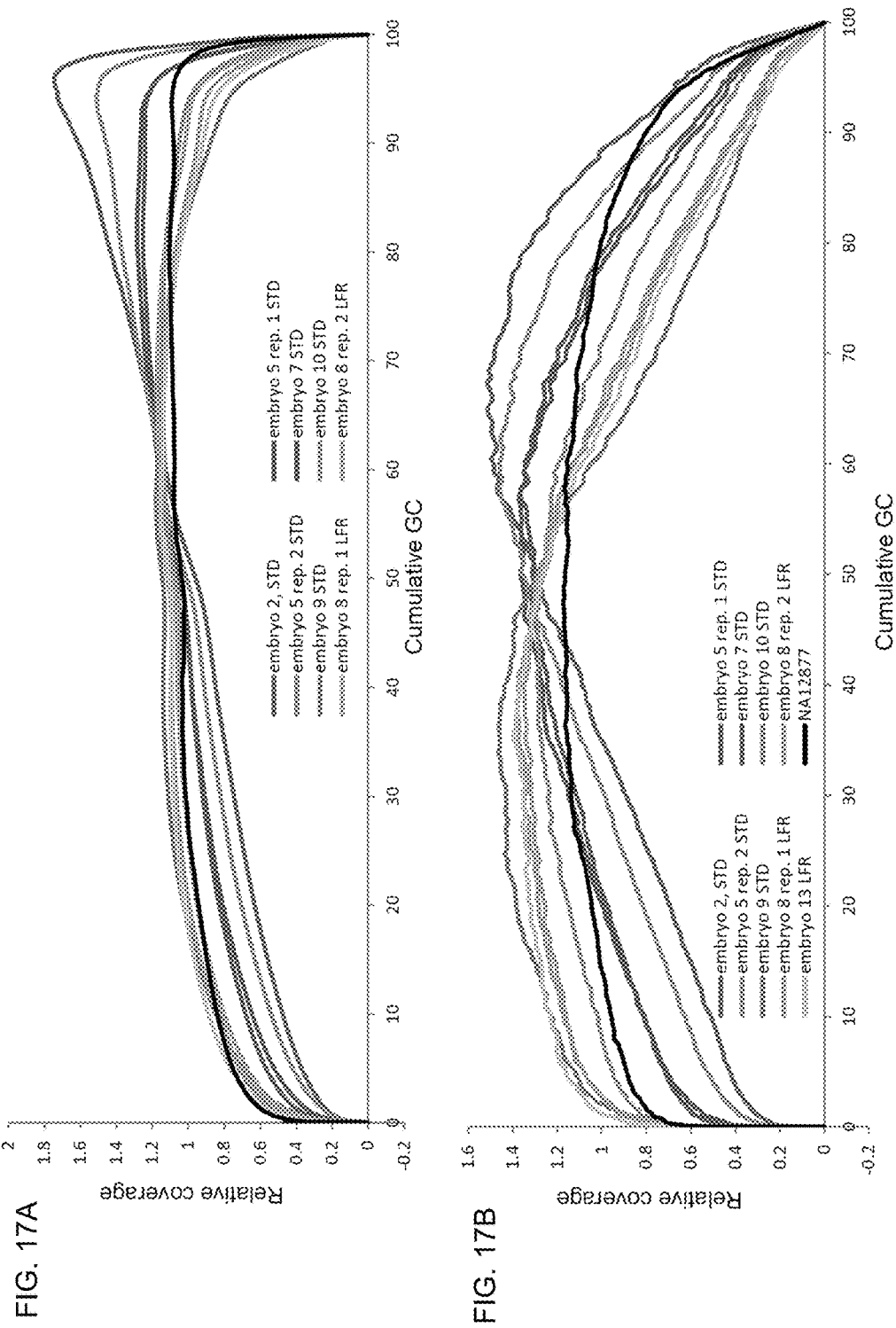
FIGS. 17A and 17B show plots of coverage vs. GC content for various embryo samples according to embodiments of the present invention.

Second, a noticeable bias in amplifying GC-rich regions of the genome was apparent in every sample as a result of MDA amplification (FIGS. 17A and 17B); a phenomenon that has previously been described [Peters, B. A. et al. 2012]. This makes some genomic regions analyzable only with 100× or greater average read coverage. In FIGS. 17A and 17B, relative coverage (normalized to haploid coverage) is provided as a function of GC content. FIG. 17A provides results for whole genome coverage. FIG. 17B provides results for exome coverage. Note that MDA-processed samples tend to have lower coverage in GC-rich regions compared to those samples sequenced by our standard process with 5 ug of genomic DNA (NA12877, in black).

B. Assessing Sensitivity and Reducing False Positive Variants in Embryo Genomes

We have previously shown that genomes assembled using highly amplified DNA have a large number of false positive single nucleotide variants (SNVs), presumably due to the error rate of polymerases. To better understand discovery and error rates, we compared results from replicate libraries of embryo #5. For this embryo there was a difference in quality between replicates; however, useful comparisons could still be made. Replicate libraries from embryo #5 shared ~87% of called heterozygous SNPs. Applying a high confidence filter to remove SNPs with low read coverage or poor mapping quality in the lower quality replicate increased the percent of shared heterozygous SNPs between replicates to over 90% (Table 3). While this strategy clearly removed false positives, it also removed ~192,000 heterozygous SNPs shared between replicates and predominantly representing true variants.

TABLE 3

|  | Rep. 2 | Shared with Rep. 1 | Not Shared with Rep. 1 | % Shared |
|---|---|---|---|---|
| All heterozygous SNPs | 1,855,779 | 1,618,554 | 237,225 | 87.2 |
| VQHIGH only | 1,576,110 | 1,426,365 | 149,745 | 90.5 |
| VQLOW only | 279,669 | 192,189 | 87,480 | 68.7 |
| VQHIGH heterozygous in Rep. 2 low or no coverage in Rep. 1 | 106,826 | | | |

Table 3 shows high confidence filter false positive SNV reduction in replicate embryo #5 libraries. Applying a high confidence filter increases the overall rate of sharing between replicate libraries from the same embryo. However, application of this filter reduces the sensitivity of detection by about 10% in these samples.

Applying this filter across all libraries reduced the total number of called SNPs in each genome by 107,000-298,000 (Table 4) and most likely reduced the ability to detect detrimental variants by ~5% on average. Table 4 shows high confidence filter reduction of SNP calls. Application of the high confidence filter reduces the total number of SNPs called in each library by 3.

While this loss in sensitivity may be acceptable in some circumstances, there remain 150,000 SNVs called as high quality in the lowest quality replicate of embryo #5 but not shared with the higher quality replicate. Around 107,000 of these can be explained as not being called or being called homozygous due to loss of one or both alleles in replicate 1 during whole genome amplification.

indels that our test fails to discover are located in homopolymer regions which are typically not found in coding or other functional regions of the genome.

TABLE 6

|  | Rep. 2 | Shared with Rep. 1 | Not Shared with Rep. 1 | % Shared |
| --- | --- | --- | --- | --- |
| Ebryo #5 | | | | |
| All heterozygous indels | 223,662 | 131,320 | 92,342 | 58.7 |
| VQHIGH only | 134,771 | 104,271 | 30,500 | 77.4 |
| VQLOW only | 88,891 | 27,049 | 61,842 | 30.4 |

TABLE 4

|  | 2A_STD | 5B_STD | 5C_STD | 7C_STD | 9B_STD | 10C_STD-12lanes |
| --- | --- | --- | --- | --- | --- | --- |
| SNP total count | 3,141,234 | 3,396,447 | 3,300,128 | 3,405,988 | 2,533,192 | 3,240,496 |
| High confidence SNP total count | 2,852,126 | 3,251,203 | 3,050,097 | 3,247,236 | 2,280,061 | 2,922,885 |
| SNPs removed by quality filter | 289,108 | 145,244 | 250,031 | 158,752 | 253,131 | 317,611 |
| % reduction in SNPs called | 10.1% | 4.5% | 8.2% | 4.9% | 11.1% | 10.9% |

|  | 10C_STD-21lanes | 10C_STD | 8A-LFR-200 | 8C-LFR-200 | 13C-LFR-200 |
| --- | --- | --- | --- | --- | --- |
| SNP total count | 3,392,896 | 3,414,314 | 3,579,628 | 3,562,218 | 3,524,479 |
| High confidence SNP total count | 3,216,337 | 3,307,510 | 3,426,247 | 3,351,395 | 3,343,716 |
| SNPs removed by quality filter | 176,559 | 106,804 | 153,381 | 210,823 | 180,763 |
| % reduction in SNPs called | 5.5% | 3.2% | 4.5% | 6.3% | 5.4% |

Most of the remaining ~43,000 SNVs are likely to be polymerase errors incorporated early in the amplification process and difficult to discern from true variants (Table 5). Without replicate libraries, these remaining false positives are difficult to identify and remove using only read and mapping quality metrics. Table 5 shows phasing improves sensitivity and removes polymerase errors. Applying LFR phasing removes potential polymerase errors that would otherwise be called high confidence heterozygous SNPs. Additionally, LFR improves sensitivity by phasing the majority of low quality SNPs that would be removed using only a quality filter.

TABLE 5

|  | Called in Rep. 2 not shared with Rep. 1 | Shared |
| --- | --- | --- |
| VQHIGH | 41,936 | 1,866,714 |
| VQHIGH and phased | 11,900 | 1,824,640 |
| VQLOW | 134,498 | 34,645 |
| VQLOW and phased | 13,931 | 30,042 |

A similar analysis was performed on insertions and deletions (indels). In general, indels are more difficult to identify and call correctly. As a result only 59% of all heterozygous indels found in replicate 2 of embryo #5 are shared with replicate 1. The percent of shared indels increases to over 77% when we apply the high confidence filter, but again reduces the sensitivity to detect all shared indels (Table 6). Table 6 shows high confidence filter false positive reduction of indels in replicate embryo libraries. Applying a high confidence filter increases the overall rate of sharing between replicate libraries from the same embryo. However, application of this filter reduces the sensitivity of detection by 12-25% in these samples. The low or no coverage criteria includes homozygous calls in replicate 1.

From the 77% rate of shared indels we estimate our indel discovery rate is 88% (0.879×0.879=0.774). The majority of TABLE 6-continued

|  | Rep. 2 | Shared with Rep. 1 | Not Shared with Rep. 1 | % Shared |
| --- | --- | --- | --- | --- |
| VQHIGH heterozygous in Rep. 2 low or no coverage in Rep. 1 | 19,715 | | | |
| Embryo #8 | | | | |
| All heterozygous indels | 301,379 | 166,246 | 135,133 | 55.2 |
| VQHIGH only | 195,328 | 147,948 | 47,380 | 75.7 |
| VQLOW only | 106,051 | 18,298 | 87,753 | 17.3 |
| VQHIGH heterozygous in Rep. 2 low or no coverage in Rep. 1 | 28,016 | | | |

C. Identifying Genes with Multiple Detrimental Variants

With extremely accurate and phased genome sequences available from four LFR libraries we set out to determine how many genes were potentially inactivated due to detrimental variants in exons and transcription factor binding sites (TFBS). We previously demonstrated [Peters, B. A. et al, Nature (2012)] that LFR phasing can be used to determine which genes have heterozygous detrimental variants on both alleles, leading to gene inactivation. In this study, we extended our analyses to include homozygous variants as we could be confident that we avoided miscalling allelic drop-outs as homozygous variants by linking those variants to the surrounding heterozygous SNPs located in phased contigs. We also included those short homozygous insertions and deletions that passed our high quality filter because the current analysis pipeline does not attempt to phase indels. We found that each embryo had more than 200 genes that appear to be inactivated due to coding variants and another 300-400 genes that are inactivated due to coding and TFBS inactivation.

Recent studies [MacArthur, D. G. & Tyler-Smith, C. Loss-of-function variants in the genomes of healthy humans. *Hum Mol Genet* 19, R125-130 (2010); MacArthur, D. G. et al. A systematic survey of loss-of-function variants in human protein-coding genes. *Science* 335, 823-828 (2012)] have shown that many inactivated genes in humans appear to have redundant functions or are not critical for a healthy existence. Removing all variants found at a frequency of 10% or more in 54 unrelated genomes sequenced by Complete Genomics, Inc. (completegenomics.com/public-data/) as well as genes found to be "loss of function tolerant" by MacArthur et al. resulted in a dramatic reduction in the number of inactivated genes that might result in a detrimental phenotype to fewer than 20 in each embryo.

Embryo #8 was found to harbor potentially detrimental variations in TTN. While these particular variations have not been previously described, similar alterations in TTN have been associated with cardiomyopathy. However, it should be noted that TTN is the longest gene in the human genome and would be expected to have a higher probability of collecting random non-detrimental variations. The remaining genes are poorly annotated and have no functional information that can be used in screening of these embryos. Furthermore, no novel protein truncating mutations are found after removing of all such variants present in 54 unrelated genomes.

Interestingly, ~30% of variants from this analysis have a highly detrimental impact on one of the ~4 million ENCODE project annotated TFBSs [Neph, S. et al. An expansive human regulatory lexicon encoded in transcription factor footprints. *Nature* 489, 83-90 (2012); Thurman, R. E. et al. The accessible chromatin landscape of the human genome. *Nature* 489, 75-82 (2012)]. Neph et al have suggested that there may be as many as ~6 million additional TFBSs in the human genome. Taken together there may be >10 additional genes affected in these embryos that are missed in this analysis due to lack of proper annotation. Repeating this analysis on an LFR library prepared in a similar fashion from 5 leukocytes from an anonymous donor shows similar numbers of affected genes, suggesting that these embryos are no different from a normal individual.

The 10% frequency threshold may exclude disease causing variants with high frequency in some populations; many of these have already been identified and can be analyzed separately.

D. Analysis of Rare Family and De Novo Variants

Overall, we show that this advanced comprehensive WGS analysis is able to find thousands of phased rare family variants and de novo mutations (not present in 54 public genomes) in coding and regulatory genomic regions of IVF embryos (e.g., 3280 variants in replicate 1 of embryo #8). Only a few of these variants (~0.1%) appear to be potentially detrimental as compound heterozygotes with other variants with minor allele frequencies <10% in our 54 public genomes. This demonstrates the sensitivity and specificity of this WGS process in providing comprehensive PGD. The compound detrimental annotation may be too conservative and some of the 143 of 3280 variants found detrimental may seriously affect health despite affecting only one chromosome. However, most of these variants likely represent a substantial part of the carrier burden.

E. High Resolution Copy Number Variant (CNV) Analysis

Detecting variations at single-base resolution is critical for a truly comprehensive PGD test, but just as important is proper quantification of gains and losses of multi-base regions of the genome. Analyzing read coverage by position across the genome allows this type of information to be generated from standard libraries. Unfortunately, as discussed above, a large amount of read coverage variability was introduced by the amplification required to make standard libraries from embryos (FIG. 15), allowing for only very large amplifications and deletions to be detected. LFR libraries also required a similar amount of amplification, resulting in the same read coverage variability across the genome (FIG. 15).

However, we can use the fact that each well of an LFR library typically contains just one fragment from any genomic region to convert the variable read coverage into a signal of presence or absence of that particular region. Despite this reduction in noise, many regions of the genome have fluctuating fragment coverage, likely due to losses during LFR library processing steps and false read mapping. In these instances, we can use phasing information to measure coverage for each haplotype independently.

By examining the ratio between haplotypes we can be much more confident in calling CNVs (FIG. 10). Using this information we were able to identify greater than 100 regions that were clearly lost in each embryo. Of these deletions, several removed short exons in one parental chromosome in each embryo. In each case the remaining allele was screened for detrimental heterozygous SNPs using the criteria for finding inactivated genes above. No additional detrimental variants were found suggesting that these genes should each have one active copy. We performed the same analysis on the healthy control leukocyte library and found similar numbers of mostly different CNVs and deleted exons.

VI. MATERIALS AND METHODS

A. Embryo Methods Summary

Following conventional ovarian stimulation and egg retrieval, eggs were fertilized by intracytoplasmic sperm injection (ICSI) to avoid sperm contamination in the PGD test. Following growth to day 3, embryos were biopsied using fine glass needles and one cell was removed from each embryo. Each blastomere was added individually to a clean tube, covered with molecular-grade oil and shipped on ice to Reprogenetics, Inc. (Livingston, N.J.) for PGD. The samples were processed immediately upon arrival using a test designed to PCR amplify the mutation of a CTG trinucleotide repeat expansion in the gene DMPK1 and two linked markers. Following the clinical PGD testing and embryo transfer, unused blastocyst-stage embryos were donated to the NYU Fertility Center (New York, N.Y.) and shared with Reprogenetics for use in developing new PGD testing modalities. Patients were informed of the research and all work was undertaken with full approval by an IRB from the collaborating centre.

Up to 10 cells were biopsied from each embryo, frozen, and shipped to Complete Genomics, Inc. (Mountain View, Calif.) for advanced WGS analysis. A modified multiple displacement amplification (MDA) [Dean, F. B. et al. 2002] was employed to generate sufficient template DNA for whole genome sequence analysis using Complete Genomics' DNA nanoarray sequencing platform. Briefly, isolated cells from each blastocyst were lysed and DNA was alkaline denatured with the addition of 1 ul of 400 mM KOH/10 mM EDTA. After 1 minute, thio-protected random 8mers were added to denatured DNA. The mixture was neutralized after 2 minutes with 1 ul of 400 mM HCl/600 mM Tris-HCl and a master mix containing final concentrations of 50 mM Tris-HCl (pH 7.5), 10 mM $MgCl_2$, 10 mM $(NH_4)_2SO_4$, 4 mM DTT, 250 uM dNTPs (USB, Cleveland, Ohio), and 12 units of phi29 polymerase (Enzymatics, Beverly, Mass.) was added to make a total reaction volume of 100 ul. The MDA reaction was incubated for 45 minutes at 37° C. and inactivated at 65° C. for 5 minutes. Approximately 2 ug of DNA was generated by the MDA reaction for WGS analysis. LFR libraries were processed in a manner similar to above except denatured DNA was first separated into each well of a 384 well plate prior to whole genome amplification and a few additional steps, as previously described [Peters, B. A. et al. 2012] were performed after amplification. Genomic data was mapped and phased as previously described [Peters, B. A. et al. 2012; Drmanac, R. et al. 2010; and Carnevali, P. et al. 2011].

B. Single Pixel Imaging

The current Complete Genomics' platform uses patterned arrays of DNA nano-balls with a spacing of 600 nm center to center. A single 1"×3" microscope slide has ~4 billion DNA spots. To take advantage of the patterned DNA grid for fast imaging, a CCD camera is aligned with the DNA arrays so that each spot is read with one CCD pixel for each of four colors. This yields the theoretical maximum imaging efficiency for massively parallel genomic sequencing. At ~70 bases per spot with a 60% total yield, one array generates >50× coverage of a human genome per slide (4B spots×0.6 yield×70 bases/spot/3 Gb genome).

C. Methods of Genomic Variant Annotation

In order to annotate variants identified in these sequencing libraries, variant (VAR) files from both our LFR phasing algorithm and from the standard Complete Genomics output were first merged together to form a larger VAR file. Quality scores for variants were inherited from the standard output VAR file whenever available. This data set was then further annotated with gene descriptions and coding regions using NCBI Genbank *Homo sapiens* genome assembly release version 37.1 as a parameter file.

A selection program was used to identify the genes with variants likely to be detrimental. Detrimental variants fall into two broad categories: (I) those variants that change the amino acid sequence or intron/exon structure; and (II) changes affecting the transcription start site or transcriptional regulation.

Category I variants fall into 2 sub-categories:
1) Variants causing a frameshift, nonstop, splicesite or nonsense mutation in the amino acid sequence.
2) Variants causing an amino acid missense mutation that causes a significant change to a protein using PolyPhen2.

II variants were identified using ENCODE motif model detection. We used the 683 ENCODE motif models to search through 8,374,968 published DNase I footprints. Each of these DNase I footprints belongs to one of 2,890,742 larger DNase I hypersensitive sites (DHS), and each DHS represents a promoter region linked to a specific gene; thus, we can link any variant affecting an ENCODE-defined motif to a likely effect on transcription of a certain gene. We annotated any variant causing a decrease in motif score of ≥4 as detrimental.

Genes containing 2 or more detrimental variants are grouped into 2 classes:

Class 1. Both Category I variants. All detrimental variants in this class with scores above the threshold are scored as equally detrimental. This class contains two sub-classes:
Class 1.1. The 2 detrimental variants are located on the same allele, based on assembly and phasing data.
Class 1.2. The 2 detrimental variants are located on two different alleles based on assembly and phasing data. Presumably, genes in this subcategory are the most deleterious, as these variants result in a complete lack of wild type protein.

Class 2. Genes with at least 2 detrimental variants, one of which is a Category I variant, and the other is located within an ENCODE DNase I footprint, as predicted by the hidden Markov models (HMM). The impact of the variant is computed based on HMM model scores. Class 2 contains two sub-classes:
Class 2.1. The 2 detrimental variants are located on the same allele, based on assembly and phasing data.
Class 2.2. The 2 detrimental variants are located on two different alleles based on assembly and phasing data.

VII. COMPUTER SYSTEM

Figure 18:
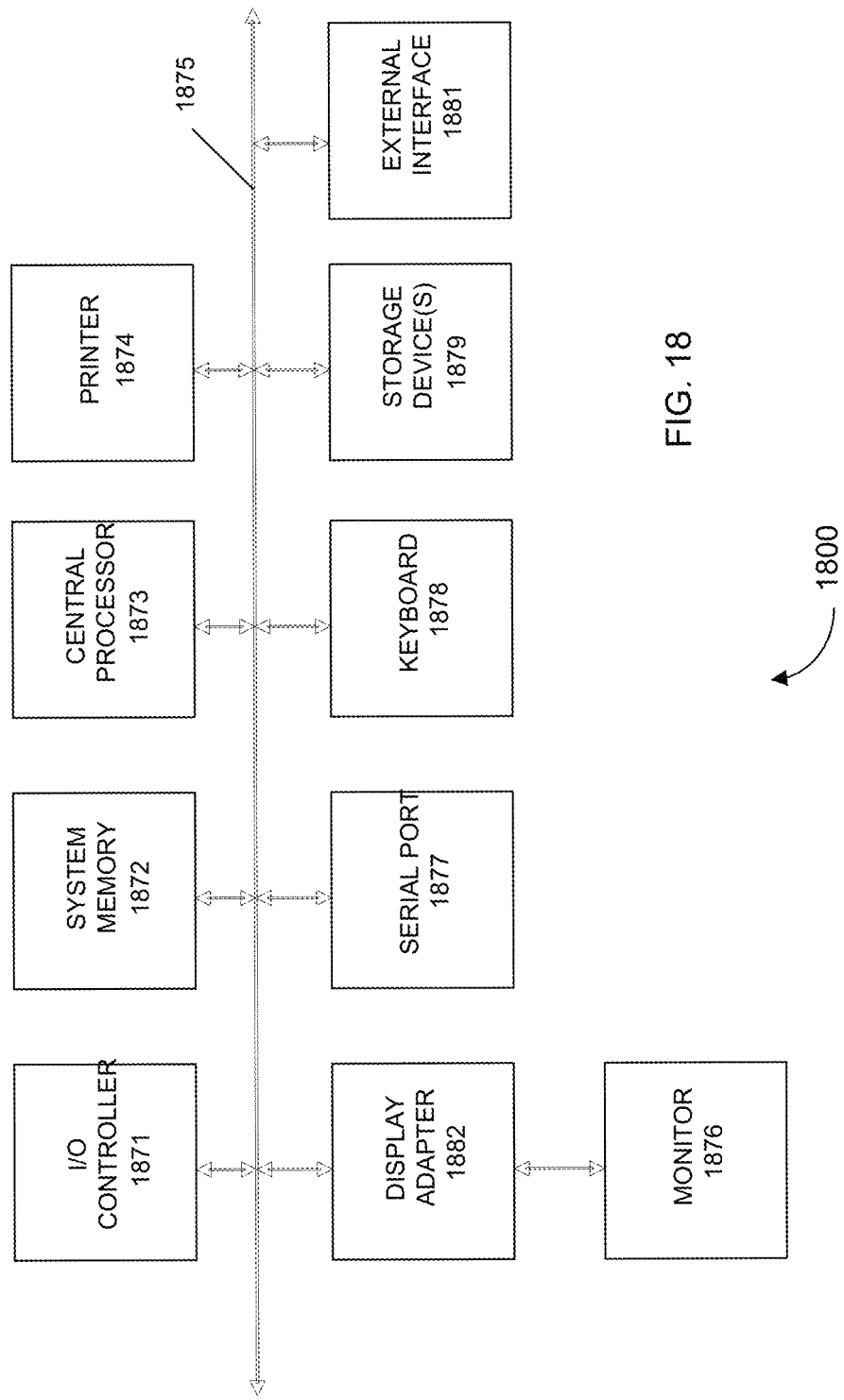
FIG. 18 shows a block diagram of an example computer system 1800 usable with system and methods according to embodiments of the present invention.

Any of the computer systems mentioned herein may utilize any suitable number of subsystems. Examples of such subsystems are shown in FIG. 18 in computer apparatus 1800. In some embodiments, a computer system includes a single computer apparatus, where the subsystems can be the components of the computer apparatus. In other embodiments, a computer system can include multiple computer apparatuses, each being a subsystem, with internal components.

The subsystems shown in FIG. 18 are interconnected via a system bus 1875. Additional subsystems such as a printer 1874, keyboard 1878, storage device(s) 1879, monitor 1876, which is coupled to display adapter 1882, and others are shown. Peripherals and input/output (I/O) devices, which couple to I/O controller 1871, can be connected to the computer system by any number of means known in the art, such as serial port 1877. For example, serial port 1877 or external interface 1881 (e.g. Ethernet, Wi-Fi, etc.) can be used to connect computer system 1800 to a wide area network such as the Internet, a mouse input device, or a scanner. The interconnection via system bus 1875 allows the central processor 1873 to communicate with each subsystem and to control the execution of instructions from system memory 1872 or the storage device(s) 1879 (e.g., a fixed disk, such as a hard drive or optical disk), as well as the exchange of information between subsystems. The system memory 1872 and/or the storage device(s) 1879 may embody a computer readable medium. Any of the data mentioned herein can be output from one component to another component and can be output to the user.

A computer system can include a plurality of the same components or subsystems, e.g., connected together by external interface 1881 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware (e.g. an application specific integrated circuit or field programmable gate array) and/or using computer software with a generally programmable processor in a modular or integrated manner. As user herein, a processor includes a multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C# or scripting language such as Perl or Python using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of exemplary embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

A recitation of "a", "an" or "the" is intended to mean "one or more" unless specifically indicated to the contrary.

All patents, patent applications, publications, and descriptions mentioned here are incorporated by reference in their entirety for all purposes. None is admitted to be prior art.

The following are references referred to above.

What is claimed is:

1. A method of resolving a base at a genomic position of a haplotype of an organism from a sample obtained from the organism, the method comprising:
    attaching labels to a plurality of nucleic acid molecules of a plurality of larger nucleic acid molecules of the organism;
    fragmenting the plurality of larger nucleic acid molecules to obtain the plurality of nucleic acid molecules, wherein different labels correspond to different larger nucleic acid molecules;
    sequencing the plurality of nucleic acid molecules of the organism;
    receiving, at a computer system, sequence data from the sequencing of the plurality of nucleic acid molecules of the organism, wherein the sequence data for each of the plurality of nucleic acid molecule includes:
        one or more sequence reads of at least one portion of the nucleic acid molecule, and
        a label corresponding to the one or more sequence reads, the label indicating a larger nucleic acid molecule that is an origin of the nucleic acid molecule;
    for each of the plurality of nucleic acid molecules:
        mapping, by the computer system, at least one sequence read of the nucleic acid molecule to a reference genome;
    identifying a first plurality of first hets, each first het having a respective first allele and a respective second allele;
    determining, by the computer system, a phasing of the first alleles and the second alleles of the first plurality of first hets to determine a first contig, the first contig specifying the first alleles as corresponding to a first haplotype and specifying the second alleles as corresponding to a second haplotype,
    linking, by the computer system, a first locus to the first contig, the linking including:
        identifying at least two of the first hets that have a sequence read sharing a label with a sequence read that maps to the first locus; and
    resolving a first base to be at a first genomic position of the first locus for the first haplotype of the first contig, the resolving based on the first base being at the first genomic position on a plurality of locus sequence reads, each sharing a label with at least one het sequence read that includes a first allele of the first haplotype, wherein the het sequence reads cover the at least two of the first hets.

2. The method of claim 1, wherein at least one of the sequence reads mapping to the first locus includes a base that is different than the reference genome at the first genomic position.

3. The method of claim 1, wherein the linking includes:
    for each haplotype, calculating a sum of counts of shared labels across the first hets for a plurality of base calls at the first locus.

4. The method of claim 1, wherein the resolving uses only locus sequence reads that share a label with het sequence reads from at least a minimum number of hets, the minimum number being greater than one.

5. The method of claim 1, further comprising:
identifying a first number of shared labels, each shared label corresponding to:
one or more sequence reads mapping to the first locus, and
at least one sequence read mapped to at least one first het of the first contig, the first locus not being one of the first plurality of first hets; and
linking, by the computer system, the first locus to the first contig based on the first number of shared labels being greater than a threshold number of labels.

6. The method of claim 5, wherein each shared label corresponds to at least one sequence read mapping to at least a minimum number of hets, the minimum number being larger than one.

7. The method of claim 5, wherein the first number of shared labels includes a count of a label for each first het that shares a label with a sequence read of the first locus.

8. The method of claim 5, wherein the at least one first het of the first contig is within a threshold distance from an end of the first contig.

9. The method of claim 5, further comprising:
dynamically determining the threshold number of labels, wherein the threshold number of labels is dynamically determined based on one or more of: a number of cells in the sample, a number of possible labels, an amount of nucleic acid molecules corresponding to a label, and a depth of sequencing performed.

10. The method of claim 1, wherein the first hets are within a specified distance of the first locus.

11. The method of claim 1, further comprising:
using the first contig to link to the first locus based on an identification that the first contig is within a window around the first locus.

12. The method of claim 11, further comprising:
using the first contig to link to the first locus based on an identification that the first contig satisfies one or more criteria.

13. The method of claim 12, wherein the one or more criteria include the first contig being the longest contig within the window around the first locus.

14. The method of claim 1, further comprising:
identifying a second plurality of second hets, each second het having a respective first allele and a respective second allele;
determining, by the computer system, a phasing of the first and second alleles of the second plurality of second hets to determine a second contig, the second contig specifying the first alleles as corresponding to the first haplotype and specifying the second alleles as corresponding to the second haplotype;
linking the first locus to the second contig, wherein het sequence reads including at least one first allele of the first haplotype for both the first contig and the second contig are used to resolve the first base; and
connecting the first and second contigs using the first locus.

15. The method of claim 1, wherein the sequence reads mapping to the first locus include a plurality of different alleles at the first genomic position, the method further comprising:
resolving a second base to be at the first genomic position for the second haplotype of the first contig based on the second base being at the first genomic position on locus sequence reads that each shares a label with a het sequence read including a second allele of the second haplotype, the second base being different than the first base.

16. The method of claim 15, wherein the plurality of different alleles include at least three alleles, and wherein a third allele is identified as being an error based on the third allele being at the first genomic position on sequence reads that share labels with one or more het sequence reads that include a first allele of the first haplotype and with one or more het sequence reads that include a second allele of the second haplotype.

17. The method of claim 16, wherein a number of sequences reads with the third allele is less than a sum of a number of sequence reads with first base calls and the number of sequence reads with second base calls.

18. The method of claim 1, further comprising:
resolving the first base to be at the first genomic position for the second haplotype based on the first base being at the first genomic position on locus sequence reads that each shares a label with a het sequence read including a second allele of the second haplotype, wherein the first genomic position is determined to be a homozygous variant.

19. The method of claim 1, wherein the first locus is identified as having at least one no-call prior to resolving, and wherein the resolving changes the no-call to the first base.

20. The method of claim 1, wherein the determination of the first contig is based on the labels corresponding to sequence reads mapped to the first hets.

21. The method of claim 1, wherein determining the phasing of the first and second alleles of the first plurality of first hets to determine the first contig is performed by reading the phasing from a file.

22. The method of claim 1, wherein identifying the first plurality of first hets is based on quality scores determined from any one or more of: a mapping of sequence reads to the first hets, base calling of sequence reads mapped to the first hets, and assembly of sequence reads covering the first hets.

23. The method of claim 1, wherein the plurality of nucleic acid molecules are obtained from a fragmenting of the plurality of larger nucleic acid molecules, wherein the plurality of larger nucleic acid molecules are distributed among a plurality of aliquots in which the fragmenting occurs, and wherein the label of a nucleic acid molecule indicates which aliquot the nucleic acid molecule is from.

* * * * *